United States Patent
Stewart et al.

(10) Patent No.: US 6,346,387 B1
(45) Date of Patent: Feb. 12, 2002

(54) DETECTION OF BINDING REACTIONS USING LABELS DETECTED BY MEDIATED CATALYTIC ELECTROCHEMISTRY

(75) Inventors: David H. Stewart, Durham; John W. Groelke, Raleigh; H. Holden Thorp, Carrboro; Allen E. Eckhardt, Durham, all of NC (US)

(73) Assignees: Xanthon, Inc., Research Triangle Park; The University of North Carolina at Chapel Hill, Chapel Hill, both of NC (US)

(*) Notice: Subject to any disclaimer, the term of this patent is extended or adjusted under 35 U.S.C. 154(b) by 0 days.

(21) Appl. No.: 09/722,065

(22) Filed: Nov. 24, 2000

Related U.S. Application Data

(63) Continuation-in-part of application No. 09/603,217, filed on Jun. 26, 2000, which is a division of application No. 09/179,665, filed on Oct. 27, 1998, now Pat. No. 6,132,971, which is a division of application No. 08/667,338, filed on Jun. 20, 1996, now Pat. No. 5,871,918, which is a continuation-in-part of application No. 08/495,817, filed on Jun. 27, 1995, now abandoned, and a continuation-in-part of application No. 09/267,552, filed on Mar. 12, 1999, now Pat. No. 6,180,346, which is a continuation-in-part of application No. 08/667,338, filed on Jun. 20, 1996, now Pat. No. 5,871,918, which is a continuation-in-part of application No. 08/495,817, filed on Jun. 27, 1995.

(51) Int. Cl.$^7$ .......................... C12Q 1/68; C12P 19/34; C07H 21/02; A61B 5/05

(52) U.S. Cl. .................. 435/6; 435/91.2; 435/91.5; 435/91.51; 536/23.1; 600/345; 935/6

(58) Field of Search .................. 435/6, 91.2, 91.5, 435/91.51; 536/23.1; 600/345; 935/6, 17, 77, 78

(56) References Cited

U.S. PATENT DOCUMENTS

| | | | |
|---|---|---|---|
| 4,545,382 A | 10/1985 | Higgins et al. | 600/347 |
| 4,683,202 A | 7/1987 | Mullis | 435/6 |
| 4,704,353 A | 11/1987 | Humphries et al. | 205/777.5 |
| 4,800,159 A | 1/1989 | Mullis et al. | 435/6 |
| 4,840,893 A | 6/1989 | Hill et al. | 435/6 |
| 4,883,579 A | 11/1989 | Humphries et al. | 204/403 |
| 4,908,307 A | 3/1990 | Rodland et al. | 435/6 |
| 4,945,045 A | 7/1990 | Forrest et al. | 435/25 |
| 4,963,815 A | 10/1990 | Hafeman | 205/777.5 |
| 4,965,188 A | 10/1990 | Mullis et al. | 435/6 |
| 5,066,372 A | 11/1991 | Weetall | 205/777.5 |
| 5,108,889 A | 4/1992 | Smith | 435/4 |
| 5,112,974 A | 5/1992 | Barton | 546/4 |
| 5,143,854 A | 9/1992 | Pirrung et al. | 453/6 |
| 5,157,032 A | 10/1992 | Barton | 514/185 |
| 5,171,853 A | 12/1992 | Thorp et al. | 536/26.1 |
| 5,175,082 A | 12/1992 | Jeffreys | 435/6 |
| 5,194,372 A | 3/1993 | Nagai et al. | 435/6 |
| 5,272,056 A | 12/1993 | Burrows et al. | 435/6 |
| 5,278,043 A | 1/1994 | Bannwarth et al. | 536/23.1 |
| 5,312,527 A | 5/1994 | Mikkelsen et al. | 205/777.5 |
| 5,378,628 A | 1/1995 | Grätzel et al. | 204/403 |
| 5,405,783 A | 4/1995 | Pirrung et al. | 436/518 |
| 5,439,829 A | 8/1995 | Anderson et al. | 436/518 |
| 5,532,129 A | 7/1996 | Heller | 435/6 |
| 5,565,322 A | 10/1996 | Heller | 435/6 |
| 5,605,662 A | 2/1997 | Heller et al. | 422/88.1 |
| 5,632,957 A | 5/1997 | Heller et al. | 422/68.1 |
| 5,871,918 A | 2/1999 | Thorp et al. | 435/6 |
| 5,968,745 A | 10/1999 | Thorp et al. | 435/6 |
| 6,127,127 A | 10/2000 | Eckhardt et al. | 435/6 |

FOREIGN PATENT DOCUMENTS

| | | |
|---|---|---|
| EP | 0 478 319 A1 | 4/1992 |
| WO | WO 85/02627 | 6/1985 |
| WO | WO 91/15768 | 10/1991 |
| WO | WO 93/20230 | 10/1993 |
| WO | WO 94/22889 | 10/1994 |
| WO | WO 95/00530 | 1/1995 |
| WO | WO 97/02359 | 1/1997 |
| WO | WO 98/35232 | 8/1998 |

OTHER PUBLICATIONS

Abstract, Khrapko, K.R., et al., Hybridization of DNA with oligonucleotides immobilized in gel: convenient method for detection of single base changes, *Mol. Biol.* (1991).

Armistead, Paul M., et al., Modification of Indium Tin Oxide Electrodes with Nucleic Acids: Detection of Attomole Quantities of Immobilized DNA by Electrocatalysis, *Analytical Chemistry*, vol. 72, No. 16, pp. 3764–3770 (2000).

Thorp, H. Holden, Cutting out the middleman: DNA biosensors based on electrochemical oxidation, *TIB Tech*, vol. 16 (Mar. 1998).

Brabec, Viktor, et al., Electrochemical Behaviour of Proteins at Graphite Electrodes: I. Electrooxidation of Proteins as a New Probe of Protein Structure and Reactions, *Biochimica et Biophysica Acta*, vol. 625, pp. 43–50 (1980).

(List continued on next page.)

*Primary Examiner*—Jeffrey Fredman
*Assistant Examiner*—Arun Kr. Chakrabarti
(74) *Attorney, Agent, or Firm*—Myers Bigel Sibley & Sajovec

(57) ABSTRACT

A method of detecting binding interactions and target molecules, such as proteins, protein fragments, recombinant proteins, recombinant protein fragments, extracellular matrix proteins, ligands, carbohydrates, steroids, hormones, drugs, drug candidates, immunoglobulins and receptors of eukaryotic, prokaryotic or viral origin, by mediated electrochemistry using labels that react with transition metal mediator complexes in a detectable catalytic redox reaction. These labels are attached directly to binders, target molecules, surrogate target molecules, or to affinity ligands capable of binding to the target or to surrogate target molecules capable of competing with the target for binding to another binder. The labels can be naturally present (endogenous) in the binder, target or affinity ligand, or constructed by the covalent attachment of the label to the binder, target, affinity ligand or surrogate target (exogenous).

112 Claims, 6 Drawing Sheets

OTHER PUBLICATIONS

Reynaud, J.A., et al., 359—The Electrochemical Oxidation of Three Proteins: RNAase A, Vobine Serum Albumin and Concanavalin A at Solid Electrodes, *J. Electroanal. Chem,* vol. 116, pp. 595–606 (1980).

DeFelippis, Michael R., et al., Pulse Radiolytic Measurement of Redox Potentials: The Tyrosine and Tryptophan Radicals, *Biochemistry,* vol. 28, pp. 4847–4853 (1989).

Brabec, V., et al., 434—Electrochemical Behaviour of Proteins at Graphite Electrodes, Part II. The Effect of Protein Adsorption, *Bioelectrochemistry and Bioenergetics,* vol. 8, pp. 451–458 (1981).

Elbicki, Janean M., et al., Ultrafiltration of Human Serum to Determine the Size of Species that Poison Voltammetric Electrodes, *Biosensors,* vol. 4, pp. 251–257 (1989).

DiGleria, K., et al., Site-specific introduction of an electroactive label into a non–electroactive enzyme (β–lactamase I), *FEBS Letters,* vol. 400, pp. 155–157 (1997).

Wagenknecht, Hans–Achim, et al., Evidence of Electron Transfer from Peptides to DNA: Oxidation of DNA–Bound Tryptophan Using the Flash–Quench Technique, *American Chemical Society,* vol. 122, No. 1, pp. 1–7 (Jan. 12, 2000).

Pikulski, Michael, et al., Iridium–Based Electrocatalytic Systems for the Determination of Insulin, *Anal. Chem.,* vol. 72, pp. 2696–2702 (2000).

Brazill, Sara A., et al., Detection of Native Amino Acids and Peptides Utilizing Sinusoidal Voltammetry, *Anal. Chem.,* vol. 72, pp. 5542–5548 (2000).

Strosberg, A. Donny, et al., Receptor–based assays, *Current Opinion in Biotechnology,* vol. 2, pp. 30–36 (1991).

Testa, Ugo, et al., The Transferrin Receptor, *Critical Reviews in Oncogenesis,* vol. 4, No. 3, pp. 241–276 (1993).

Assay of Plasma Insulin in Human Subjects by Immunological Methods, *Nature,* vol. 184, pp. 1648–1649 (Nov. 12, 1959).

Tijssen, P., *Practice and Theory of Enzyme Immunoassays* (1985).

Guyda, Harvey J., et al., Heterogeneity of Human Growth Hormone and Prolactin Secreted in Vitro: Immunoassay and Radioreceptor Assay Correlations, *JCE&M,* vol. 41, No. 5, pp. 953–967, 1975.

Najjam, Saloua, et al., Characterization of Human Recombinant Interleukin 2 Binding to Heparin and Heparan Sulfate Using an Elisa Approach, *Cytokine,* vol. 9, No. 12, pp. 1013–1022 (Dec. 1997).

Mould, A. Paul, Solid Phase Assays for Studying ECM Protein–Protein Interactions, *Methods in Molecular Biology,* vol. 139, pp. 295–299 (2000).

McGown, Linda B., et al., The Nucleic Acid Ligand: A New Tool for Molecular Recognition, *Anal. Chem.,* vol. 67, pp. 663A–668A, 199.

Ullrich, Axel, et al., Signal Transduction by Receptors by Tyrosine Kinase Activity, *Cell,* vol. 61, pp. 203–212 (Apr. 20, 1990).

Baxter, Robert C., Insulin–like growth factor (IGF)–binding proteins: interactions with IGFs and intrinsic bioactivities, *Am. J. Physiol. Endocrinol. Metab.,* vol. 278, pp. E967–E976 (2000).

Schöneberg, Torsten, et al., Structural basis for G protein–coupled receptor function, *Molecular and Cellular Endocrinology,* vol. 151, pp. 181–193 (1999).

Schryvers, Anthony B., et al., Bacterial Lactoferrin Receptors, *Advances in Lactoferrin Research,* pp. 123–133 (1998).

Modun, Belinda J., et al., The *Staphylococcus aureus* and *Staphylococcus epidermidis* transferring–binding proteins are expressed in vivo during infection, *Microbiology,* vol. 144, pp. 1005–1012 (1998).

Domingo, E., et al., Biochemical and structural studies with neutralizing antibodies raised against foot–and–mouth disease virus, *Virus Research,* vol. 62, pp. 169–175 (1999).

Bella, Jordi, et al., Review: Rhinoviruses and Their ICAM Receptors, *Journal of Structural Biology,* vol. 128, pp. 69–74 (1999).

Bains, William, The chip of the 90s, *Chemistry in Britain,* pp. 122–125 (Feb. 1995).

Carter, Michael T., et al., Voltammetric Studies of the Interaction of Metal Chelates with DNA. 2. Tris–Chelated Complexes of Cobalt(III) and Iron(II) with 1,10–Phenanthroline and 2,2'–Bipyridine, *American Chemical Society,* vol. 111, pp. 8901–8911 (1989).

Chee, Mark, et al., Accessing Genetic Information with High–Density DNA Arrays, *Science,* vol. 274, pp. 610–614, (Oct. 25, 1996).

Daube, G., et al., Typing of *Clostridium perfringens* by in vitro amplification of toxin genes, *Journal of Applied Bacteriology,* vol. 77, pp. 650–655 (1994).

Du, Zijin, et al., Automated Fluorescent DNA Sequencing of Polymerase Chain Reaction Products, *Methods in Enzymology,* vol. 218, pp. 104–121 (1993).

Fedorova, Olga S., et al., Application of Tris(2,2'–bipyridyl)ruthenium(III) for the Investigation of DDNA Spatial Structure by a Chemical Modification Method, *Journal of Inorganic Biochemistry,* vol. 34, pp. 149–155 (1988).

Fodor, Stephen P.A., et al., Multiplexed biochemical assays with biological chips, *Nature* vol. 364, pp. 555–556 (Aug. 5, 1993).

Fodor, Stephen P.A., et al., Light–Directed, Spatially Addressable Parallel Chemical Synthesis, *Science,* vol. 251, pp. 767–773 (Feb. 15, 1991).

Guatelli, John C., et al., Isothermal, in vitro amplification of nucleic acids by a multienzyme reaction modeled after retroviral replication, *Proc. Natl. Acad. Sci. USA,* vol. 87, pp. 1874–1878 (Mar. 1990).

Hall, Jennifer M., et al., An Electrochemical Method for Detection of Nucleic Acid Hybridisation, *Biochemistry and Molecular Biology International,* vol. 32, No. 1, pp. 21–28 (Jan. 1994).

Holodniy, Mark, et al., Determination of Human Immunodeficiency Virus DNA in Plasma and Cellular Viral DNA Genotypic Zidovudine Resistance and Viral Load during Zidovudine–Didanosine Combination Therapy, *Journal of Virology,* vol. 69, No. 6, pp. 3510–3516 (Jun. 1995).

Jenkins, Yonchu et al., A Sequence–Specific Molecular Light Switch: Tethering of an Oligonucleotide to a Dipyridophenazine Complex of Ruthenium (II), *J. Am. Chem. Soc.,* vol. 114, pp. 8736–8738 (1992).

Johnston, Dean H., et al., Trans–Dioxorhenium(V)–Mediated Electrocatalytic Oxidation of DNA at Indium Tin–Oxide Electrodes: Voltammetric Detection of DNA Cleavage in Solution, *Inorg. Chem.,* vol. 33, pp. 6388–6390 (1994).

Johnston, Dean H., et al., Electrochemical Measurement of the Solvent Accessibility of Nucleobases Using Electron Transfer between DNA and Metal Complexes, *J. Am. Chem. Soc.,* vol. 117, pp. 8933–8938 (1995).

Kwoh, Deborah Y., et al., Target amplification systems in nucleic acid–based diagnostic approaches, *Americal Biotechnology Laboratory*, vol. 8, No. 13, pp. 14–25 (Oct. 1990).

Kwoh, D. Y., et al., Transcription–based amplification system and detection of amplified human immunodeficiency virus type 1 with a bead–based sandwich hybridization format, *Proc. Natl. Acad. Sci. USA*, vol. 86, pp. 1173–1177 (Feb. 1989).

Lewis, Ricki, PCR's Competitors Are Alive and Well and Moving Rapidly Towards Commercialization, *Genetic Engineering News*, (Jun. 1, 1992).

Lishanski, Alla, et al., Mutation detection by mismatch binding protein, MutS, in amplified DNA: Application to the cystic fibrosis gene, *Proc. Natl. Acad. Sci. USA*, vol. 91, pp. 2674–2678 (Mar. 1994).

Lizardi, Paul M., et al., Exponential Amplification of Recombinant–RNA Hybridization Probes, *Bio/Technology*, vol. 6, pp. 1197–1202 (Oct. 1988).

Lulitanond, Viraphong, et al., Detection of herpes simplex virus type 2 Bgl II N fragment in paraffin–embedded cervical tissue sections using nested polymerase chain reaction, *Molecular and Cellular Probes*, vol. 8, pp. 441–447 (1994).

Maeder, Marcel, et al., Nonlinear Least–Squares Fitting of Multivariate Absorption Data, *Anal. Chem.* vol. 62, pp. 2220–2224 (1990).

Maher, III, L. James, Inhibition of T7 RNA Polymerase Initiation by Triple–Helical DNA Complexes: A Model for Artificial Gene Repression, *Biochemistry*, vol. 31, No. 33, pp. 7587–7594 (1992).

Marchand–Brynaert, Jacqueline, et al., Surface Functionalization of Poly(ethylene terephthalate) Film and Membrane by Controlled Wet Chemistry: Chemical Characterization of Carboxylated Surfaces, *Journal of Colloid and Interface Science*, vol. 173, pp. 236–244 (1995).

Martin, W. John, Infectious Diseases, *The Polymerase Chain Reaction*, pp. 406–417 (1994).

Meade, Thomas J. et al., Electron Transfer through DNA: Site–Specific Modification of Duplex DNA with Ruthenium Donors and Acceptors, *Angew. Chem. Int. Ed. Engl.*, vol. 34, No. 3, pp. 352–354 (1995).

Millan, Kelly M., et al., Sequence–Selective Biosensor for DNA Based on Electroactive Hybridization Indicators, *Analytical Chemistry*, vol. 65, No. 17, pp. 2317–2323 (1993).

Millan, Kelly M., et al., Voltammetric DNA Biosensor for Cystic Fibrosis Based on a Modified Carbon Paste Electrode, *Anal. Chem.*, vol. 66, pp. 2943–2948 (1994).

Murphy, C. J., et al., Long–Range Photoinduced Electron Transfer Through a DNA Helix, *Science*, vol. 262, pp. 1025–1029 (Nov. 12, 1993).

Murphy, Catherine, J., et al., Fast photoinduced electron transfer through DNA intercalation, *Proc. Natl. Acad. Sci. USA*, vol. 91, pp. 5315–5319 (Jun. 1994).

Neubauer, Andrease, et al., Prognostic Importance of Mutations in the RAS Proto–Oncogenes in De Novo Acute Myeloid Leukemia, *Blood*, vol. 83, No. 6, pp. 1603–1611 (Mar. 15, 1994).

Nielsen, Peter E., et al., Sequence–Selective Recognition of DNA by Strand Displacement with a Thymine–Substituted Polyamide, *Science*, vol. 254, pp. 1497–1500 (Dec. 6, 1991).

Noble, Deborah, DNA Sequencing on a Chip: Compact arrays of probes may be used for ultrafast DNA sequencing if fabrication and interpretation problems can be solved, *Analytical Chemistry*, vol. 67, No. 5, pp. 201A–204A (Mar. 1, 1995).

Osteryoung, Janet, Voltammetry for the Future, *Acc. Chem. Res.*, vol. 26, No. 3, pp. 77–83 (1993).

Pyle, A.M, et al., Mixed–Ligand Complexes of Ruthenium(II): Factors Governing Binding to DNA, *J. Am. Chem. Soc.*, vol. 111, pp. 3051–3058 (1989).

Ried, Thomas, et al., Simultaneous visualization of seven different DNA probes by in situ hybridization using combinatorial fluorescence and digital imaging microscopy, *Proc. Natl. Acad. Sci. USA*, vol. 89, pp. 1388–1392 (Feb. 1992).

Rudolph, Manfred, et al., A Simulator for Cyclic Voltammetric Responses, *Analytical Chemistry*, vol. 66, No. 10, pp. 589A–600A (May 15, 1994).

Saleeba, Jennifer A., et al., Chemical Cleavage of Mismatch to Detect Mutations, *Methods in Enzymology*, vol. 217, pp. 286–296 (1993).

Satyanarayan, S., et al., Neither Δ–nor Λ–Tris(phenanthroline)ruthenium(II) Binds to DNA by Classical Intercalation, *Biochemistry*, vol. 31, No. 39, pp. 9319–9324 (Oct. 6, 1992).

Schena, Mark, et al., Quantitative Monitoring of Gene Expression Patterns with a Complementary DNA Microarray, *Science*, vol. 270, pp. 467–470 (Oct. 20, 1995).

Mellors, John W., et al., Prognosis in HIV–1 Infection Predicted by the Quantity of Virus in Plasma, *Science*, vol. 272, pp. 1167–1170 (May 24, 1996).

Spargo, C.A., et al., Chemiluminescent detection of strand displacement amplified DNA from species comprising the Mycobacterium tuberculosis complex, *Molecular and Cellular Probes*, vol. 7, pp. 395–404 (1993).

Steenken, S., et al., One–Electron–Reduction Potentials of Pyrimidine Bases, Nucleosides, and Nucleotides in Aqueous Solution. Consequences for DNA Redox Chemistry, *J. Am. Chem.*, vol. 114, pp. 4701–4709 (1992).

Strobel, Scott A., et al., Site–Specific Cleavage of Yeast Chromosome by Oligonucleotide–Directed Triple–Helix Formation, *Science*, pp. 73–75 (Jul. 6, 1990).

Strobel, Scott A., et al., Minor Groove Recognition of the Conserved G–U Pair at the Tetrahymena Ribozyme Reaction Site, *Science*, vol. 267, pp. 675–679 (Feb. 3, 1995).

Titball, Richard W., et al., Molecular Cloning and Nucleotide Sequence of the Alpha–Toxin (Phospholipase C) of *Clostridium perfringens*, *Infection and Immunity*, vol. 57, No. 2, pp. 367–376 (Feb. 1989).

Tizard, Richard, et al., Imaging of DNA sequences with chemiluminesecence, *Proc. Natl. Acad. Sci. USA*, vol. 87, pp. 4514–4518 (Jun. 1990).

Tracy, M.A., et al., Dynamics of Rigid and Semirigid Rodlike Polymers, *Annu. Rev. Phys. Chem.*, vol. 43, pp. 525–557 (1992).

Walker, G. Terrance, et al., Strand displacement amplification—an isothermal, in vitro DNA amplification technique, *Nucleic Acids Research*, vol. 20, No. 7, pp. 1691–1696 (1992).

Want, Joseph, et al., Electrochemical Measurements of Oligonucleotides in the Presence of Chromosomal DNA Using Membrane–Covered Carbon Electrodes, *Anal. Chem.* vol. 69, pp. 4056–4059 (1997).

Waring, M.J., Complex Formation between Ethidium Bromide and Nucleic Acids, *J. Mol. Biol.*, vol. 13, pp. 269–282 (1965).

Weiss, Rick, Hot Prospect for New Gene Amplifier: Ligase chain reaction, a combination DNA amplifier and genetic screen, could do for DNA diagnostics what PCR has done for basic molecular biology, *Science*, vol. 254, pp. 1292–1923 (Nov. 29, 1991).

DETECTION OF BINDING REACTIONS USING LABELS DETECTED BY MEDIATED CATALYTIC ELECTROCHEMISTRY

CROSS-REFERENCE TO RELATED APPLICATIONS

This is a continuation-in-part of co-pending application Ser. No. 09/603,217, filed Jun. 26, 2000, which is a divisional application of application Ser. No. 09/179,665, filed Oct. 27, 1998, now U.S. Pat. No. 6,132,971, which is a divisional application of application Ser. No. 08/667,338, filed Jun. 20, 1996, now U.S. Pat. No. 5,871,918, which is a continuation-in-part of application Ser. No. 08/495,817, filed Jun. 27, 1995; now abandoned and a continuation-in-part of co-pending application Ser. No. 09/267,552 filed Mar. 12, 1999, now U.S. Pat. No. 6,180,346 which is a continuation-in-part of application Ser. No. 08/667,338, filed Jun. 20, 1996, now U.S. Pat. No. 5,871,918, which is a continuation-in-part of application Ser. No. 08/495,817, filed Jun. 27, 1995; each of which is incorporated herein by reference.

BACKGROUND OF THE INVENTION

1. Field of the Invention

The present invention relates to the detection of biological substances through binding interactions and, in particular, to methods of detecting proteins and other substances by mediated catalytic electrochemistry.

2. Description of the Related Art

For many reasons, researchers are interested in the detection of biological substances such as nucleic acids, proteins, and carbohydrates. Detection of such biomolecules can allow for identification and development of targets for drug discovery and gene expression analysis. The electrochemical detection of nucleic acids provides an alternative to fluorescent and radiochemical detection techniques that potentially eliminates the need for labeling.

The parent applications of the instant application, whose entire specifications, drawings, and claims are specifically incorporated herein by reference, disclose, among other inventions, sequencing and methods of qualitatively and quantitatively detecting nucleic acid hybridization. Such inventions represent a major advance in the art and provide oxidation-reduction reactions that function in a catalytic manner without the addition of an enzyme or fluorescent label. These catalytic reactions are useful for determining the presence or absence of nucleic acids and provide for extremely accurate testing of biological samples. More specifically, catalytic oxidation has been found to be useful for quantitative detection of preselected nucleic acid bases (U.S. Pat. No. 5,871,918). The disclosures of each of the patents and publications referred to herein are incorporated herein by reference.

The technology described in U.S. Pat. No. 5,871,918 utilizes the discovery that nucleotide bases of DNA can be electrochemically oxidized using transition metal complexes as mediators. In this system, the nucleotide bases function as an array of endogenous redox-active labels that allow for ultrasensitive detection of DNA in conjunction with microelectrode methods. The detection reaction follows a two-step mechanism involving reversible oxidation/reduction of the mediator. First the mediator is oxidized by an electrode. Then, the mediator is reduced by the preselected nucleotide base and reoxidized at the electrode. In order for mediated oxidation of nucleic acids to proceed efficiently, the mediator and nucleotide base should have similar oxidation potentials. For example, catalytic oxidation of guanine can be carried out using the mediator, ruthenium$^{2+}$ (2,2'-bipyridine)$_3$ (Ru(bpy)$_3^{2+}$). In solution, Ru(bpy)$_3^{2+}$ exhibits a reversible redox couple at 1.05 V (vs. Ag/AgCl reference), similar to the oxidation potential observed for guanine (about 1.1 V vs. Ag/AgCl). Thus, addition of guanine-containing DNA to a solution of Ru(bpy)$_3^{2+}$ leads to catalytic enhancement in the electrochemical oxidation current via the following reaction sequence:

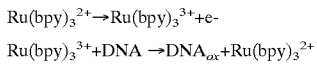

where DNA$_{ox}$ represents a DNA molecule in which guanine has undergone a one electron oxidation.

The regeneration of reduced Ru(bpy)$_3^{2+}$ by reaction with guanine creates a catalytic cycle in which the presence of DNA is detected by transfer of electrons from the preselected base to the electrode. The number of turnovers obtained in the catalytic cycle depends on the number of electrons in the preselected base that can be oxidized by the mediator and the number of preselected bases. In the case of guanine oxidation, Ru(bpy)$_3^{2+}$ is capable of oxidizing guanine by at least two electrons (Armistead, P. M. and Thorp, H. H., *Anal. Chem.* 2000, 72, 3764), and some reports suggest as many as 30 electrons obtained from guanine through overoxidation steps (Thorp, H. H., *Trends Biotechnol.* 1998, 16, 117). A typical DNA molecule will contain on average about one guanine every four bases so even a small oligonucleotide will have multiple guanines available for catalytic turnover of Ru(bpy)$_3^{2+}$. As a result of these properties, detection of nucleic acids via mediated catalytic electrochemistry is an extremely sensitive method.

Thus, in one embodiment of the prior invention, a nucleic acid sample is contacted with an oligonucleotide probe, which possesses a sequence, at least a portion of which is capable of binding to a known portion of the sequence in the nucleic acid sample, to form a hybridized nucleic acid, after which the hybridized nucleic acid is reacted with a suitable mediator, which is capable of oxidizing a preselected nucleic acid base in the hybridized nucleic acid sample in an oxidation-reduction reaction.

The selection of mediator in this prior work is dependent upon the particular preselected nucleotide base chosen, and is readily determinable by those skilled in the art. Particularly preferred mediators include transition metal complexes that are capable of participating in electron transfer with the preselected base such that the reduced form of the metal complex is regenerated, completing a catalytic cycle. An example of a suitable transition metal complex is Ru(bpy)$_3^{2+}$; however, the mediator or oxidizing agent may be any molecule such as a cationic, anionic, non-ionic, or zwitterionic molecule that is reactive with the preselected base at a unique oxidation potential to transfer electrons from the nucleic acid to the electrode. All that is required is that the mediator be reacted with the hybridized nucleic acid sample under conditions sufficient to achieve the selective oxidation of the preselected base.

The oxidation-reduction rate is detected, for example, with a detection electrode, and the electronic signal may be detected by cyclic voltammetry or other means known in the art. Hybridized DNA target contains guanine and is therefore more redox-active than the probe strand, which preferably is either selected or designed to contain a minimal number of guanines.

In U.S. Pat. No. 5,968,745 of Thorp et al., a polymer-electrode is provided that is useful for the electrochemical detection of a preselected base in a nucleic acid. The polymer-electrode comprises: (a) a substrate having a conductive working surface; and (b) a polymer layer on the conductive working surface. The polymer layer has a plurality of microfluidic reaction openings distributed throughout the layer. An oligonucleotide probe is preferably bound to the polymer layer.

U.S. Pat. No. 6,127,127 provides a self-assembled phosphonate monolayer, which in the preferred embodiment is a carboxy-alkyl phosphonate, on an ITO surface. The oligonucleotide probe is immobilized on an electrode surface modified by the self-assembled monolayer. The electrode with the self-assembled monolayer is useful for the electrochemical detection of a preselected base in a nucleic acid and for determining the presence of a target nucleic acid in a sample, by contacting the self-assembled monolayer with the sample, so that the target nucleic acid and the oligonucleotide probe form a hybridized nucleic acid on the monolayer; reacting the hybridized nucleic acid with a transition metal complex capable of oxidizing a preselected base in the hybridized nucleic acid in an oxidation-reduction reaction; detecting the oxidation-reduction reaction; and determining the presence or absence of the target nucleic acid from the detected oxidation-reduction reaction.

In both the polymer-electrode and monolayer patents, determination of the presence of a target protein in a sample can also be achieved and comprises attaching a protein-binding substance to a polymer-electrode or self-assembled monolayer on a conductive working surface according to the invention; exposing the polymer-electrode or monolayer to the sample; exposing the polymer-electrode or monolayer to a second protein-binding substance that has been modified to contain an oligonucleotide label; reacting the polymer-electrode or monolayer with a transition metal complex capable of oxidizing a preselected base in the oligonucleotide label in an oxidation-reduction reaction; detecting the oxidation-reduction reaction; and determining the presence or absence of the target protein from the detected oxidation-reduction reaction. The polymer-electrode or monolayer may be brought into contact with the conductive working surface of the substrate either before or after reacting the polmer-electrode or monolayer with the first protein binding substance. The target protein may be modified to contain an oligonucleotide label as is known in the art.

Amino acids, such as tyrosine and tryptophan, have been detected by direct, unmediated electrochemistry (Brabec, V. and Mornstein, V., *Biochimica et Biophysica Acta*, 1980, 625, 43; Renaud, J. A. et al., *Bioelectrochem. & Bioenergetics*, 1980, 7, 395). However, the levels of current obtained by direct, unmediated oxidation of amino acids are generally low, on the order of a few microamps for concentrated solutions of amino acids (100 $\mu$M).

Oxidation potentials of several amino acids have been determined using thermodynamic and kinetic methods (DeFilippis, M. R. et al., *Biochem.*, 1989, 28, 4857). The oxidation potential for tyrosine is about 0.6–0.73 V (vs. Ag/AgCl reference), and the oxidation potential for tryptophan is about 0.6–0.85 V (vs. Ag/AgCl). Other amino acid oxidation potentials have been estimated for histidine (1.1–1.4 V), cysteine (0.5–0.8 V), methionine (0.9–1.2 V), and cystine (1.1–1.2 V)(Brabec, V. and Mornstein, V., *Biochimica et Biophysica Acta*, 1980, 625, 43; Renaud, J. A. et al., *Bioolectroehem. & Bioenergetics*, 1980, 7, 395), but the extent to which these amino acids are oxidized depends on the electrode material.

It has been observed that proteins can be adsorbed to electrodes at both negative and positive potentials through an electrostatic interaction when the protein net charge is opposite that of the electrode (Brabec, V. et al., *Bioelectrochem. & Bioenergetics*, 1981, 8, 451). Although the adsorption is initiated by an electrostatic interaction, it has been found that adsorption in this manner leads to the formation of a protein that is irreversibly adsorbed to the electrode surface. This phenomenon can interfere with electrochemical detection at electrodes because the adsorbed protein blocks the electrode surface. Thus, in attempts to detect protein in solution directly, Brabec et al. found that the adsorbed protein fouled the electrode surface so that fresh protein molecules could not reach the surface and interfered with protein detection at the electrode. Along these same lines, Elbicki et al. (Elbicki, J. et al., *Biosensors*, 1989, 4, 251) have found that the removal of proteins from samples is necessary to protect electrode surfaces from fouling.

Because of the low sensitivity and poor selectivity of direct electrochemical detection of proteins, attempts have been made to use exogenous labels to facilitate this electrochemical detection. In one example, DiGleria et al. sought to convert a "redox-inactive" protein to a "redox-active" protein by adding an exogenous redox-active label to the enzyme $\beta$-lactamase (DiGleria, K. et al., *FEBS Letters*, 1997, 400, 155). This approach involved engineering the enzyme to contain an unnatural cysteine residue and then modifying this residue with a thiol-reactive ferrocene compound, N-(2-ferrocene-ethyl)maleimide.

Previous work with metal complexes and amino acids includes the study of one-electron oxidation of tryptophan by ruthenium-DNA intercalator compounds (Wagenknecht, H.-A. et al., *J. Amer. Chem. Soc.*, 2000, 122, 1). This process is not catalytic, however, and was initiated by light rather than by an applied electrochemical potential. Also, in this system, electron transfer between tryptophan and the ruthenium complex was found to be dependent on guanine as an intermediate. In another study, the one-electron oxidation of a reference redox couple, osmium$^{2+}$ (2,2'-bipyridine)$_3$ (Os(bpy)$_3$), was used to determine the redox potentials of tryptophan and tyrosine by pulse radiolysis (DeFilippis, M. R. et al. *Biochem.*, 1989, 28, 4857), but in this case, Os(bpy)$_3^{2+}$ acted as a reductant of an oxidized amino acid. Therefore, a two-step catalytic oxidation reaction between oxidized transition metal complex and the amino acid was not present in this prior work.

Recently, Pikulski and Gorski have suggested the catalytic oxidation of disulfide bonds and the amino acid cystine by the iridium complex, Ir(H$_2$O)$_2$Cl$_2$ (Pikulski, M. et al., *Anal. Chem.*, 2000, 72, 2696). This chemistry has been utilized to create a flow injection sensor for detecting insulin, in which the mediator is immobilized in an oxide layer on a glassy carbon electrode and the insulin is in solution. A related method has been proposed for detecting amino acids and peptides in solution at copper electrodes using catalytic electrochemistry (Brazill, S. A. et al., *Anal. Chem.*, 2000, 72, 5542). Although not fully understood, the detection process is believed to involve amino acid oxidation by Cu(III) in a conductive oxide or hydroxide layer that is formed under alkaline conditions. In both the work of Pikulski et al. and Brazill et al., the metal complex is a solid phase mediator in the electrode to which the analyte diffuses nonspecifically. Thus, the electrode is only capable of detecting analytes that come into direct contact with the electrode. The electrochemical detection utilized in the above methods is distinct from the mediated electrochemical detection methods of the instant invention wherein there is a nonconductive layer and wherein the mediator is a soluble, freely diffusible transition metal complex that is capable of oxidizing labels on binders that are bound to the electrode via biological binding interactions (antibody-protein, receptor-ligand, DNA-protein, and protein-protein).

A means of detecting protein binding has been disclosed in the PCT application of Fowlkes and Thorp using a soluble transition metal complex mediator and biomolecules labeled with transition metal complexes including $Ru(bpy)_3^{2+}$ and $Os(bpy)_3^{2+}$ (PCT/US98/02440). The basic mechanism of this detection scheme involves electron transfer from the label to an electrode via the soluble mediator. The electrochemical current enhancement obtained from the label is limited by the number of electrons in the label that can be oxidized by the soluble mediator so the oxidation of the mediator is limited to only one cycle per label for $Ru(bpy)_3^{2+}$ and $Os(bpy)_3^{2+}$. The method of Fowlkes and Thorp is distinctly different from the technology described in this application in that the electrochemical label is a transition metal complex in Fowlkes and Thorp, whereas the present invention provides a different label. When the electrochemical label is a transition metal complex, the number of cycles of mediated electron transfer is generally limited to one per label.

Measurement of a target protein was first achieved by Yalow and Berson (Yalow, R. S. and Berson, S. A., *Nature*, 1959, 184, 1648) using a competitive, radiolabeled ligand immunoassay (i.e., RIA) for the protein insulin. Since then numerous other labels have been employed in immunoassays such as enzymes, chemiluminescent and fluorescent labels, metal atoms, transition metal complexes and particles (i.e., polystyrene, gold) to measure selected target proteins (Tijssen, P., In: Laboratory Techniques in Biochemistry and Molecular Biology, 1985, Vol. 15. Elsevier Science Publishers, N.Y. 549 p). More recently, numerous other types of macromolecules other than immunoglobulins such as cell receptors (Guyda, H. J., *J. Clin. Endocrinol. Metab.*, 1975, 41, 953; Strosberg, A. D., et al., *Curr. Opin. Biotechnol.*, 1991, 2, 30), proteoglycans (Najjam, S., *Cytokine*, 1997, 9, 1013), extracellular matrix proteins (Mould, A. P., *Meth. Mol Biol.*, 2000, 139, 295) and nucleic acids (McGown L. B., et al., *Anal. Chem.*, 1995, 67, 663A) have been used as affinity binders in assays to detect target proteins. The instant invention to be described herein has the ability to utilize all the above molecular interactions to detect preselected target proteins as well as other binding substances by using peptide/amino acid or oligonucleotide labels in assays with catalytic transition metal mediated electrochemical detection.

Recently developed protein detection assay systems are commercially available from IGEN (Gaithersburg, Md.) and Luminex (Austin, Tex.). However, each of these systems is readily distinguishable from the present invention since they are dependent upon the teachings of electrochemiluminescence (IGEN) or fluorescent bead sorting (Luminex).

It is an object of this invention to detect binding interactions. The detection methodology involves oxidation of labels using transition metal mediator complexes in a detectable catalytic redox reaction and applies generally to binding interactions of immunoglobulins, receptors, proteins, and oligonucleotides with proteins, protein fragments, ligands, carbohydrates, drugs, drug candidates, steroids, hormones, and other substances. The labels are attached directly to the binders, target molecules, surrogate target molecules or to binders capable of binding targets or surrogate target molecules that compete with the target for binding. The labels can be naturally attached in the target, surrogate target, or binder (i.e., endogenous) or constructed by the covalent attachment of the label to the target, binder, or surrogate target (i.e., exogenous). Preferred labels include peptides and oligonucleotides. Preferred types of binding affinities to be utilized in the instant invention to detect target substances are based on antibody—antigen, receptor (eukaryotic, prokaryotic or viral)—ligand, DNA—protein, drug target—drug, and protein—protein interactions.

It is a further object of this invention to use detected binding interactions between specific biomolecules to determine their presence (or absence) in test samples, such as clinical samples, environmental samples, pharmaceutical samples and others. It is an additional object of this invention to determine the impact of specific drugs on the detected binding interactions between biomolecules.

Other objects and advantages will be more fully apparent from the following disclosure and appended claims.

SUMMARY OF THE INVENTION

The invention herein provides a method of detecting binding interactions and target molecules, such as proteins, protein fragments, recombinant proteins, recombinant protein fragments, extracellular matrix proteins, ligands, carbohydrates, steroids, hormones, drugs, drug candidates, immunoglobulins and receptors of eukaryotic, prokaryotic or viral origin, by mediated electrochemistry using labels that react with transition metal mediator complexes in a detectable catalytic redox reaction. These labels are attached directly to binders, target molecules, surrogate target molecules, or to affinity ligands capable of binding to the target or to surrogate target molecules capable of competing with the target for binding to another binder. The labels can be naturally present (endogenous) in the binder, target or affinity ligand, or constructed by the covalent attachment of the label to the binder, target, affinity ligand or surrogate target (exogenous). The biological binding interactions detected with this technology include antibody-antigen, protein-protein, protein-nucleic acid, drug target-drug, and receptor-ligand interactions.

Other objects and features of the inventions will be more fully apparent from the following disclosure and appended claims.

BRIEF DESCRIPTION OF THE DRAWINGS

FIG. 2A: #1, PVA block only; #2, mouse IgG→PVA block; #3, mouse IgG→PVA block→first binder; #4, mouse IgG→PVA block→first binder→second binder. FIG. 1B: #1, PVA block only; #2 human IgG→PVA block; #3, human IgG→PVA block→first binder; #4, human IgG→PVA block→first binder→second binder.

FIG. 4A: #1, PVA block only; #2, rabbit anti-beta chain hCG IgG→PVA block; #3, rabbit anti-beta chain hCG IgG→PVA block→no hCG→goat anti-alpha chain hCG IgG labeled with peptide; #4, rabbit anti-beta chain hCG IgG→PVA block→100 ng/ml hCG→goat anti-alpha chain hCG IgG labeled with peptide. FIG. 4B: #1, PVA block only; #2, rabbit anti-beta chain hCG IgG→PVA block; #3, rabbit anti-beta chain hCG IgG→PVA block→no hCG→goat anti-alpha chain hCG IgG; #4, rabbit anti-beta chain hCG IgG→PVA block→100 ng/ml hCG→goat anti-alpha chain hCG IgG.

FIG. 5A: #1, PVA block only; #2, rabbit anti-goat IgG→PVA block; #3, rabbit anti-goat IgG→PVA block→goat IgG-WOH; FIG. 5B: #1, PVA block only; #2, rabbit IgG (non-immune)→PVA block; #3, rabbit IgG (non-immune)→PVA block→goat IgG-WOH; FIG. 5C: #1, PVA block only; #2, rabbit anti-goat IgG→PVA block; #3, rabbit anti-goat IgG→PVA block→goat IgG.

DETAILED DESCRIPTION OF THE INVENTION AND PREFERRED EMBODIMENTS THEREOF

Figure 1:
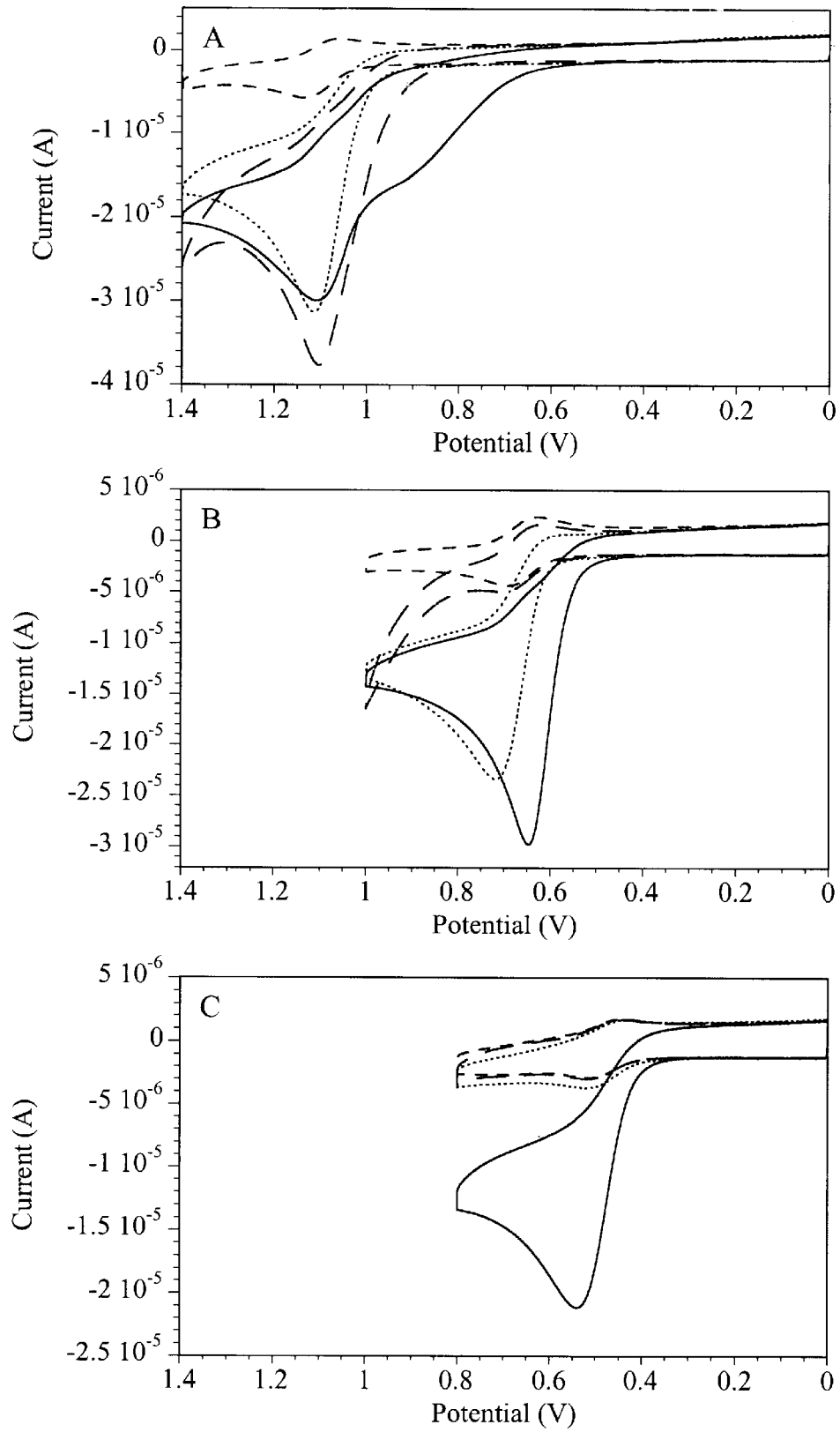
FIGS. 1A–1C. Electrochemical detection of amino acids in solution using mediated catalytic electrochemistry. Cyclic voltammograms (300 mV/s) were collected of three different transition metal mediators (FIG. 1A: $Ru(bpy)_3^{2+}$, FIG. 1B: $Os(bpy)_3^{2+}$ and FIG. 1C: $Os(Me_2\text{-bpy})_3^{2+}$) at a concentration of 20 µM in 50 mM phosphate buffer, pH 7.5 in the presence of 100 µM tryptophan (—, —), 100 µM tyrosine ( . . . ), 100 µM 5-hydroxytryptophan (— , —), or no amino acid (— — —).

The present invention provides a method of detecting binding interactions by mediated electrochemistry using labels that react with transition metal mediator complexes in a detectable catalytic redox reaction. These labels are attached directly to binders, target molecules, surrogate targets, or affinity binders capable of binding to the target or to surrogate targets. The labels can be naturally present (endogenous) in the binder, target or affinity ligand, or constructed by the covalent attachment of the label to the binder, target, affinity ligand or surrogate target (exogenous). In the present invention such exogenous labels may be oligonucleotides or peptides containing amino acids capable of being oxidized in an oxidation-reduction reaction. Most preferably, such a peptide label contains one or more amino acids capable of being oxidized in an oxidation-reduction reaction at approximately ≦0.6V, and the transition metal mediator is osmium$^{2+}$(4,4'-dimethyl-2,2'-bipyridine)$_3$.

The biological binding interactions detected with this technology include but are not limited to antibody-antigen, protein-protein, protein-nucleic acid, drug target-drug, and receptor-ligand interactions. The binding interactions can be detected in several formats including sandwich, competitive, and target-bound assays. The target substance can generally be any substance that one might wish to detect, generally being selected from the group consisting of proteins, protein fragments, ligands, carbohydrates, drugs, drug candidates and hormones. The specific target substance for a particular assay will depend on the nature of that assay. Thus, for an assay geared to smaller molecules, such as for drugs or drag candidates, a competitive assay might be preferred, while for an assay geared to larger molecules, a sandwich assay might be preferred.

As discussed in more detail below, the invention utilizes an electrode comprising a conductive substrate modified with a non-conductive layer, through which non-conductive layer a transition metal complex can transfer electrons to the conductive substrate. The electrode further comprises a member of a biological binding pair immobilized to the electrode, which member of the biological binding pair is capable of specifically binding another specific biological binder. The nonconductive layer may be the immobilized binder or a separate non-conductive layer on which the binder may be immobilized as is known in the art. For some uses, the nonconductive layer may be selected from the group consisting of streptavidin, avidin, protein A, protein G, and antibodies. It may also be a silane molecule covalently attached to the conductive substrate, said silane molecule further being capable of forming a covalent bond with the binder. The nonconductive layer to which the binder is immobilized may comprise one or more components.

Following is a summary of the various preferred embodiments of the invention, after which is a detailed discussion of components of the invention. In particular, the invention herein includes a first embodiment for a method of determining the presence or absence of a target substance in a test sample, comprising:

a) providing an electrode comprising a conductive substrate modified with a non-conductive layer having an immobilized first binder capable of binding the target substance and through which layer a transition metal mediator can freely move to transfer electrons to the conductive substrate;
  b) contacting the immobilized first binder with the test sample to form a target complex if the target substance is present in the test sample;
  c) contacting the first binder or the target complex, if present, with a second binder capable of binding the target substance and having an endogenous or exogenous label capable of being oxidized in an oxidation-reduction reaction;
  d) contacting the electrode, the immobilized first binder, and the target complex having the second binder, if present, with a transition metal mediator that oxidizes the label in an oxidation-reduction reaction between the transition metal mediator and the label, from which label there is electron transfer to the transition metal mediator resulting in regeneration of the reduced form of the transition metal mediator as part of a catalytic cycle;
  e) detecting the oxidation-reduction reaction; and
  f) determining the presence or absence of the target substance in the test sample from the detected oxidation-reduction reaction.

The target substance in this embodiment of the invention is most preferably a protein. The immobilized first binder is preferably selected from the group consisting of immunoglobulins, receptors, proteins, such as an extracellular matrix protein, and oligonucleotides. The immobilized first binder may be either a synthetic or natural (e.g., of eukaryotic, prokaryotic or viral origin) molecule. The test sample and the second binder may be added to the immobilized first binder simultaneously.

In another embodiment of the invention herein, the invention is a method of determining the presence or absence of a target substance in a test sample, comprising:

a) providing an electrode comprising a conductive substrate modified with a non-conductive layer having an immobilized binder capable of binding the target substance and through which layer a transition metal mediator can freely move to transfer electrons to the conductive substrate;
  b) contacting the immobilized binder with the test sample to form a target complex if the target substance is present in the test sample;
  c) contacting the immobilized binder with an endogenously or exogenously labeled substance capable of binding with the immobilized binder, such that binding of the labeled substance is inhibited if the target complex is present, and wherein the label is capable of being oxidized in an oxidation-reduction reaction;
  d) contacting the electrode, the immobilized binder, the target substance, and the labeled substance, if present, with a transition metal mediator that oxidizes the label in an oxidation-reduction reaction between the transition metal mediator and the label, from which label there is electron transfer to the transition metal mediator resulting in regeneration of the reduced form of the transition metal mediator as part of a catalytic cycle;
  e) detecting the oxidation-reduction reaction; and
  f) determining the presence or absence of the target substance in the test sample from the detected oxidation-reduction reaction.

This embodiment is a competitive assay where the test sample and labeled substance may be added to the immobilized binder either sequentially or simultaneously. The labeled substance in this embodiment is preferably selected from the group consisting of proteins, protein fragments, recombinant proteins and recombinant protein fragments, ligands, carbohydrates, drugs, drug candidates, steroids and hormones.

In a third embodiment of the invention, the invention is a method of determining the presence or absence of a target substance in a test sample, comprising:

a) providing an electrode comprising a conductive substrate modified with a non-conductive layer having an immobilized binder capable of binding the target substance and through which layer a transition metal mediator can freely move to transfer electrons to the conductive substrate;
  b) contacting the immobilized binder with a surrogate target capable of binding with the immobilized binder to form a target complex, said surrogate target having an endogenous or exogenous label capable of being oxidized in an oxidation-reduction reaction;
  c) contacting the target complex with the test sample, so that labeled surrogate target is displaced from the immobilized binder by the target substance, if the target substance is present in the test sample;
  d) contacting the electrode, the immobilized binder, and said surrogate target, if present, with a transition metal mediator that oxidizes the label in an oxidation-reduction reaction between the transition metal mediator and the label, from which label there is electron transfer to the transition metal mediator resulting in regeneration of the reduced form of the transition metal mediator as part of a catalytic cycle;
  e) detecting the oxidation-reduction reaction; and
  f) determining the presence or absence of the target substance in the test sample from the detected oxidation-reduction reaction.

This embodiment of the invention utilizes a surrogate target having an endogenous or exogenous label, and the surrogate target is preferably selected from the group consisting of proteins, protein fragments, recombinant proteins and recombinant protein fragments, ligands, carbohydrates, drugs, drug candidates, steroids and hormones.

In a fourth embodiment of the invention herein, the invention is a method of determining the presence or absence of a target substance in a test sample comprising:
  a) providing an electrode comprising a conductive substrate modified with a non-conductive layer having an immobilized target substance or an immobilized surrogate target substance, and through which layer a transition metal mediator can freely move to transfer electrons to the conductive substrate;
  b) contacting the immobilized target substance or immobilized surrogate target substance with the test sample and with an endogenously or exogenously labeled binder that will bind the target substance in the test sample such that the target substance in the test sample, if present, competes with the immobilized target substance or the immobilized surrogate target substance for the labeled binder, said label being capable of being oxidized in an oxidation-reduction reaction;
  c) contacting the electrode, the immobilized target substance or immobilized surrogate target substance, and the labeled binder, if present, with a transition metal mediator that oxidizes the label in an oxidation-reduction reaction between the transition metal mediator and the label, from which label there is electron transfer to the transition metal mediator resulting in regeneration of the reduced form of the transition metal mediator as part of a catalytic cycle;
  d) detecting the oxidation-reduction reaction; and
  e) determining the presence or absence of target substance in the test sample from the detected oxidation-reduction reaction.

The labeled binder and the test sample may be mixed prior to being added to the immobilized target substance or immobilized surrogate target substance. The nonconductive layer maybe the immobilized target substance or the immobilized surrogate target substance, or may comprise other molecules.

In a fifth embodiment of the invention herein, the invention is a method of determining the effect of a test sample on the binding interactions between two binders that are members of a binding pair, said method comprising:
  a) providing an electrode comprising a conductive substrate modified with a non-conductive layer having an immobilized first binder and through which layer a transition metal mediator can freely move to transfer electrons to the conductive substrate;
  b) contacting the immobilized first binder with the test sample;
  c) contacting the immobilized first binder with an endogenously or exogenously labeled second binder for said first binder, said label being capable of being oxidized in an oxidation-reduction reaction;
  d) contacting the electrode, the immobilized first binder, and the labeled second binder, if present, with a transition metal mediator that oxidizes the label in an oxidation-reduction reaction between the transition metal mediator and the label, from which label there is electron transfer to the transition metal mediator resulting in regeneration of the reduced form of the transition metal mediator as part of a catalytic cycle;
  e) detecting the oxidation-reduction reaction; and
  f) determining the effect of the test sample on the ability of the second binder to bind to the first binder from the detected oxidation-reduction reaction.

In this embodiment, the test sample, the first binder and the second binder may each be selected from the group consisting of proteins, protein fragments, recombinant proteins, recombinant protein fragments, extracellular matrix proteins, ligands, carbohydrates, steroids, hormones, drags, drug candidates, immunoglobulins, receptors of eukaryotic, prokaryotic or viral origin, and oligonucleotides. The test sample and labeled second binder may be added to the immobilized first binder simultaneously or the labeled second binder may be added to the immobilized first binder before the addition of the test sample to determine the effect of the test sample on the binding interactions between the first binder and the second binder.

In a sixth embodiment of the method of the invention herein, the invention is a method of determining the presence or absence of a target protein in a test sample, said target protein having an endogenous label capable of being oxidized in an oxidation-reduction reaction, comprising:
  a) providing an electrode comprising a conductive substrate modified with a non-conductive layer having an immobilized binder capable of binding the target protein and through which layer a transition metal mediator can freely move to transfer electrons to the conductive substrate;
  b) contacting the immobilized binder with the test sample to form a target complex if the target protein is present in the test sample;
  c) contacting the electrode, the immobilized binder and the target protein, if present, with a transition metal mediator that oxidizes the label in an oxidation-reduction reaction between the transition metal mediator and the label, from which label there is electron transfer to the transition metal mediator resulting in regeneration of the reduced form of the transition metal mediator as part of a catalytic cycle;
  d) detecting the oxidation-reduction reaction; and
  e) determining the presence or absence of the target protein in the test sample from the detected oxidation-reduction reaction.

In this embodiment, the target is a protein having an endogenous label.

The invention herein further comprises a labeled member of a binding pair useful for mediated catalytic electrochemistry, which comprises:
  a) a binder selected from the group consisting of proteins, protein fragments, recombinant proteins, recombinant protein fragments, extracellular matrix proteins, ligands, carbohydrates, steroids, hormones, drugs, drug candidates, immunoglobulins, receptors of eukaryotic, prokaryotic or viral origin, and oligonucleotides; and
  b) an exogenous peptide label containing one or more modified amino acids capable of being oxidized in an oxidation-reduction reaction at potentials below those of naturally occurring amino acids.

The preferred binder in this member of a binding pair is an antibody. There are at least two modified amino acids in the peptide label. In the preferred embodiment, the modified amino acids in the peptide label are selected from derivatives of tyrosine and tryptophan, such as 5-hydroxytryptophan; 3-aminotyrosine; and 3,4-dihydroxyphenylalanine.

A. Mediators and Oxidation-Reduction Reactions

The mediator that is needed to enable electron transfer may be any molecule such as a cationic, anionic, non-ionic, or zwitterionic molecule that is reactive with the electrochemical label at a unique oxidation potential to transfer electrons from the label to the electrode. It is important that the mediators used in the invention herein be selected to exhibit a reversible redox couple at about the same oxidation potential or higher than that observed for the label that is being detected. Thus, to use tyrosine or tryptophan as the label, the mediator must have an oxidation potential of about $\geq 0.65$ V or $\geq 0.8$ V vs. Ag/AgCl, respectively. Suitable mediators would be $Os(bpy)_3^{2+}$ and $Fe(bpy)_3^{2+}$, respectively. Similarly, in order to use guanine as the label, the mediator must have an oxidation potential about $\geq 1.1$ V vs. Ag/AgCl, and an appropriate mediator is $Ru(bpy)_3^{2+}$. Other examples of suitable mediators for use in the methods of the present invention are transition metal complexes, including, for example, Ruthenium$^{2+}$(2,2'-bipyridine)$_3$ ("Ru(bpy)$_3^{2+}$"); Ruthenium$^{2+}$(4,4'-dimethyl-2,2'-bipyridine)$_3$ ("Ru(Me$_2$-bpy)$_3^{2+}$"); Ruthenium$^{2+}$(5,6-dimethyl-1,10-phenanthroline)$_3$ ("Ru(Me$_2$-phen)$_3^{2+}$"); Iron$^{2+}$(2,2'-bipyridine)$_3$("Fe(bpy)$_3^{2+}$"); Iron$^{2+}$(4,4'-dimethyl-2,2'-bipyridine)$_3$("Fe(Me$_2$-bpy)$_3^{2+}$"); Iron$^{2+}$(5-chlorophenanthroline)$_3$("Fe(5-Cl-phen)$_3^{2+}$"); Iron$^{2+}$(4,4'-dimethyl-2,2'-bipyridine)(bipyridine)$_2$("Fe(Me$_2$-bpy)(bpy)$_2^{2+}$"); Iron$^{2+}$(4,4'-dimethyl-2,2'-bipyridine)$_2$(bipyridine)("Fe(Me$_2$-bpy)$_2$(bpy)$^{2+}$"); Osmium$^{2+}$(2,2'-bipyridine)$_3$("Os(bpy)$_3^{2+}$"); Osmium$^{2+}$(4,4'-dimethyl-2,2'-bipyridine)$_3$("Os(Me$_2$-bpy)$_3^{2+}$"); Osmium$^{2+}$(5-chlorophenanthroline)$_3$("Os(5-Cl-phen)$_3^{2+}$"); Osmium$^{2+}$(4,4'-dimethyl-2,2'-bipyridine)(bipyridine)$_2$("Os(Me$_2$-bpy)(bpy)$_2^{2+}$"); Osmium$^{2+}$(4,4'-dimethyl-2,2'-bipyridine)$_2$(bipyridine) ("Os(Me$_2$-bpy)$_2$(bpy)$^{2+}$"); dioxorhenium$^{1+}$phosphine; and dioxorhenium$^{1+}$pyridine ("ReO$_2$(py)$_4^{1+}$"). Some anionic complexes usefll as mediators are: Ru(bpy)((SO$_3$)$_2$-bpy)$_2^{2-}$ and Ru(bpy)((CO$_2$)$_2$-bpy)$_2^{2-}$ and some zwitterionic complexes useful as mediators are Ru(bpy)$_2$((SO$_3$)$_2$-bpy) and Ru(bpy)$_2$((CO$_2$)$_2$-bpy) where (SO$_3$)$_2$-bpy$^{2-}$ is 4,4'-disulfonato-2,2'-bipyridine and (CO$_2$)$_2$-bpy$^{2-}$ is 4,4'-dicarboxy-2,2'-bipyridine. Suitable substituted derivatives of the pyridine, bipyridine and phenanthroline groups may also be employed in complexes with any of the foregoing metals. Suitable substituted derivatives include but are not limited to 4-aminopyridine; 4-dimethylpyridine; 4-acetylpyridine; 4-nitropyridine; 4,4'-diamino-2,2'-bipyridine; 5,5'-diamino-2,2'-bipyridine; 6,6'-diamino-2,2'-bipyridine; 5,5'-dimethyl-2,2'-bipyridine; 6,6'-dimethyl-2,2'-bipyridine; 4,4'-diethylenediamine-2,2'-bipyridine; 5,5'-diethylenediamine-2,2'-bipyridine; 6,6'-diethylenediamine-2,2'-bipyridine; 4,4'-dihydroxyl-2,2'-bipyridine; 5,5'-dihydroxyl-2,2'-bipyridine; 6,6'-dihydroxyl-2,2'-bipyridine; 4,4',4"-triamino-2,2',2"-terpyridine; 4,4',4"-triethylenediamine-2,2',2"-terpyridine; 4,4',4"-trihydroxy-2,2',2"-terpyridine; 4,4',4"-trinito-2,2',2"-terpyridine; 4,4',4"-triphenyl-2,2',2"-terpyridine; 4,7-diamino-1,10-phenanthroline; 3,8-diamino-1,10-phenanthroline; 4,7-diethylenediamine1,10-phenanthroline; 3,8-diethylenediamine-1,10-phenanthroline; 4,7-dihydroxyl-1,10-phenanthroline; 3,8-dihydroxyl-1,10-phenanthroline; 4,7-dinitro-1,10-phenanthroline; 3,8-dinitro-1,10-phenanthroline; 4,7-diphenyl-1,10-phenanthroline; 3,8-diphenyl-1,10-phenanthroline; 4,7-disperamine-1,10-phenanthroline; 3,8-disperamine-1,10-phenanthroline; dipyrido[3,2-a:2',2'-c]phenazine; 4,4'-dichloro-2,2'-bipyridine; 5,5'-dichloro-2,2'-bipyridine; and 6,6'-dichloro-2,2'-bipyridine.

B. Oxidation-Reduction Reaction.

The mediator may be reacted with labels in or on the captured target, the surrogate target, or the binder under conditions sufficient to effect the oxidation-reduction reaction of the mediator with the label via a catalytic reaction. The solution in which the oxidation-reduction reaction takes place may be any suitable solution for solubilizing the components of the assay and preferably comprises water. Suitable conditions for permitting the oxidation-reduction reaction to occur will be known to those skilled in the art.

C. Detection of Oxidation-Reduction Reactions

The occurrence of the oxidation-reduction reaction of the invention may be detected according to any suitable means known to those skilled in the art. For example, the occurrence of the oxidation-reduction reaction may be detected using a detection (working) electrode to observe a change in the electrochemical signal, which is indicative of the occurrence of the oxidation-reduction reaction. An electrode suitable for the detection of labels in accordance with the methods described herein comprises a conductive substrate having a working surface thereon, and is sensitive to the transfer of electrons between the mediator and the label. The conductive substrate may be a metallic substrate or a non-metallic substrate, including semiconductor substrates. Preferably the electrode is a tin-doped indium oxide (ITO) electrode, a tin-oxide or an indium oxide electrode. Alternatively, the electrode may be of gold, carbon fiber or glassy carbon. The suitability of a particular electrode material ultimately is dependent on the utility of that material with the selected label(s) and mediator(s) at their required redox potentials. The conductive substrate may take any physical form, such as an elongate probe having a working surface formed on one end thereof, or a flat sheet having the working surface on one side thereof, for example in the wells of a microtiter plate.

In order to prepare the electrode for modification with immobilized biological binding entities, the electrode is modified with a suitable nonconductive layer. The nonconductive layer may have one or more of a number of functions including providing covalent attachment of biomolecules, blocking of nonspecific binding to the electrode, and allowing electron transfer between the mediator and the electrode and/or the mediator and the label. The nonconductive layer may be one or more of the following, for example: self-assembled monolayers (e.g., U.S. Pat. No. 6,127,127); cross-linked polymer layers; alkyl silane layers; alkylphosphonate-, alkylphosphate-, carboxyalkane-, alkanethiol-, or alkylamine-based layers; polymer membranes (as in U.S. Pat. No. 5,968,745) and/or one or more layers of biomolecules such as proteins, antibodies, biotin-binding molecules (avidin, streptavidin, neutravidin), protein A, protein G, receptors, or oligonucleotides. In the case of a nonconductive layer comprised of biomolecules, the nonconductive layer can serve as a capture layer for the binder, target protein, the surrogate target, or the affinity ligand. For example, on an electrode designed to detect human chorionic gonadotropin (hCG), the nonconductive layer could be an anti-hCG capture antibody; on an electrode designed to detect a ligand, a receptor molecule could serve as the nonconductive layer. Alternatively, the nonconductive layer can be a biomolecule that binds the capture molecule such as protein A for a capture antibody or an antibody directed against the capture molecule (i.e. an anti-streptavidin antibody for a binding assay using streptavidin as the capture molecule or an anti-receptor antibody for a receptor-based assay). Regardless of the nature of the nonconductive layer, this layer will ultimately be placed in contact with a solution containing the mediator prior to electrochemical detection.

Generally, a reference electrode and an auxiliary electrode are also placed in contact with the mediator solution in conjunction with the detection electrode. Suitable reference electrodes are known in the art and include, for example, silver/silver chloride (Ag/AgCl) electrodes, saturated calomel electrodes (SCE), and silver pseudo reference electrodes. A suitable auxiliary electrode is a platinum electrode.

The detection of the electrochemical signal produced by the catalytic oxidationreduction of labels permits the determination of the presence or absence of specific substances in a sample. As used herein, terms such as determining or detecting "the presence or absence" of a substance as used to describe the instant invention, also include quantitation of the amount of the substance. In the invention, the transition metal mediator is oxidized by an electrode. Then, the mediator is reduced by the label and then reoxidized at the electrode. Thus, there is electron transfer from the label to the transition metal mediator resulting in regeneration of the reduced form of the transition metal mediator as part of a catalytic cycle. The step of determining the presence or absence of target in a sample typically includes: (i) measuring the electrochemical signal generated by the oxidation-reduction reaction of the mediator at electrodes that are and are not capable of specifically binding the target, (ii) comparing the measured signal from the transition metal complex at both electrodes, and then (iii) determining whether or not the electrochemical signal generated from the mediator at the electrode that is capable of binding the target is essentially the same as, greater than, or less than, the electrochemical signal generated from the mediator at the electrode that does not bind the target. The step of measuring the electrochemical signal may be carried out by any suitable means. For example, the difference in electrochemical signal may be determined by comparing the electrochemical signal (such as current or charge) from electrodes which are and are not capable of binding the target at the same scan rate, mediator concentration, buffer condition, temperature, and/or electrochemical method.

The electrochemical signal associated with the oxidation-reduction reaction may be measured by providing a suitable apparatus in electronic communication with the detection electrode. A suitable apparatus is a potentiostat capable of measuring the electronic signal that is generated so as to provide an indication of whether or not a reaction has occurred between the label and the mediator. The electronic signal may be characteristic of any electrochemical method, including cyclic voltammetry, normal pulse voltammetry, chronoamperometry, and square-wave voltammetry, with chronoamperometry and cyclic voltammetry being the currently preferred forms.

In cyclic voltammetry, the potential of the electrochemical system is varied linearly from an initial potential between 0–800 mV to a final potential between 500–1600 mV at a constant scan rate (0.01 mV/s to 200 V/s). When the final potential is reached, the scan direction is reversed and the same potential range is swept again in the opposite direction. The preferred scan rate for $Ru(bpy)_3^{2+}$ is 1–20 V/s with a 0 mV initial potential and a 1400 mV final potential. The current is collected at each potential and the data is plotted as a current versus potential scan. For lower-potential mediators, such as $Os(bpy)_3^{2+}$ and $Os(Me_2\text{-}bpy)_3^{2+}$, instead of scanning from between 0–800 mV to between 500–1600 mV, it is preferable to scan from about between 0–100 mV to between 300–1000 mV (vs. a Ag/AgCl reference electrode) because of the lower redox potentials required to oxidize these mediators.

In chronoamperometry as used in the invention herein, the electrochemical system is stepped from an initial potential between 0 mV–800 mV directly to a final potential between 500–1600 mV and held there for some specified period of time (50 µs to 10 s) and the current is collected as a function of time. If desired, the potential can be stepped back to the initial potential, and the current can be collected at the initial potential as a function of time. The preferred potential step for $Ru(bpy)_3^{2+}$ is from between 0–800 mV to 1300 mV (vs. Ag/AgCl) with a collection time of from 50–1000 ms. For lower potential mediators, such as $Os(bpy)_3^{2+}$ and $Os(Me_2\text{-}bpy)_3^{2+}$, it is preferable to step from about 0–100 mV to 300–1000 mV (vs. Ag/AgCl).

In chronocoulometry, a potential step is also applied. For use in the invention herein, starting at the initial potential (0 mV–800 mV), the electrochemical system is stepped directly to the final potential (500 mV–1600 mV). The electrochemical system is held at the final potential for some specified period of time (50 µs to 10 s) and the charge is collected as a function of time. Although not presently done, if desired, the potential can be stepped back to the initial potential and the charge can be collected at the initial potential as a function of time.

The typical apparatus that would be used for the invention herein, may, for example, include a sample container for holding a fluid sample; an electrode, as described above; and a potentiostat in electronic communication with the electrode surface. In addition, the apparatus preferably comprises a first member of a binding pair, such as a capture antibody, attached to the electrode or to a nonconductive layer on the electrode surface. The invention may be used with a microelectronic device comprising a microelectronic substrate having first and second opposing faces, a conductive electrode on the first face, and an immobilized binder for the target substance on the second face sufficiently close to the first face to permit detection of an oxidation-reduction reaction on the second face. The oxidation-reduction reaction assay format may be in either: 1) a sandwich format wherein a target substance, captured by the immobilized first binder, is detected by a second labeled binder for the target substance, 2) a direct format wherein the target substance is captured by the immobilized first binder and is detected directly through labels bound to the target, 3) a competitive format using a labeled target or labeled surrogate target which competes with the target substance in the sample for binding to the immobilized binder, 4) a competitive format using a labeled binder and inmmobilized target substance with which the target substance in the sample competes for binding of the labeled binder, or 5) a binding assay format using an immobilized first binder, a second labeled binder, and a test sample which may or may not affect the interaction between the two binders.

D. Quantitating Target Binding.

The herein-described method is particularly well-suited to the quantitative detection of protein targets and other binding substances. In the case described in this section, the rate constant for oxidation of labels associated with the bound target by the mediator can be determined from the cyclic voltammogram by digital simulation. Under most conditions, this reaction will obey second-order kinetics, so the rate=k[mediator][label] where k is the rate constant that is specific for the particular label, [mediator] is the concentration of the mediator, and [label] is the concentration of label. If k and [mediator] are known, then the quantity of the label, and thus of the target, can be determined. In practice, a calibration curve for the current enhancements obtained with different quantities of standard solutions containing label is constructed so that the electrochemical signal enhancement observed for an electrode treated with a test sample can be used to obtain directly the quantity of label (and target) bound to the electrode. This quantity is then related directly to the quantity of target present in the test sample.

E. Labels

The labels utilized in the invention are selected from the group consisting of preselected peptides and preselected nucleotide bases, and may be endogenous or exogenous labels. The labels do not include transition metal complexes, which are used in the invention as mediators to transfer electrons to the conductive substrate. The labels have an oxidation potential approximately equal to or less than that of the transition metal mediator.

1. Endogenous

The method of the invention may be used to electrochemically detect targets containing endogenous labels, for example, particular amino acids in proteins. Endogenous labels are moieties that are contained naturally within any of the binding members of the assay. For the purposes of electrochemical protein detection, endogenous labels are oxidized or reduced in a catalytic reaction with a mediator. In the protein-detection system, these moieties include amino acids that are oxidized by catalytic mediated electrochemistry in the potential range of interest (600–1200 mV) and at potentials below that required for the oxidation of water. This includes cysteine, tyrosine, tryptophan, and histidine. Other amino acids are also oxidizable but not under the assay conditions described here.

Because amino acids oxidizable in the potential range of 600–1200 mV are present in most protein molecules (and hence in target molecules), proteins can be directly detected by catalytic mediated electrochemistry. This is particularly true for large proteins and proteins rich in tryptophan or tyrosine.

2. Exogenous

Exogenous labels are moieties that are added to binding members or targets by synthetic, artificial, natural, or other means. The role of exogenous labels is to impart electrochemical activity on a molecule that would otherwise be electrochemically inactive or to increase the electrochemical activity of an already active molecule. Examples of exogenous labels used for mediated catalytic electrochemical detection include peptides, peptides with modified amino acids, other proteinaceous electron donor and acceptor compounds, and oligonucleotides containing preselected nucleotide bases that undergo oxidation-reduction by mediated electrochemistry. Other electron donor or acceptor compounds that can be covalently attached to proteins may be used as labels for electrochemical detection of protein targets and other substances and would be obvious to those skilled in the art. In particular, donor compounds that are oxidized at potentials approximately $\leq 0.6$ V (vs. Ag/AgCl) are useful as labels because they can be oxidized by mediated electrochemistry under conditions in which there is no background signal from oxidation of nucleic acids or amino acids present in the assay. Examples of low-potential labels are peptides containing the modified amino acids 5-hydroxytryptophan (Examples 1,6, and 7); 3-aminotyrosine; and 3,4-dihydroxyphenylalanine. These modified amino acids each have an oxidation potential approximately $\leq 0.47$ V (vs. Ag/AgCl) and are well-suited to react in a mediated catalytic oxidation-reduction reaction with the transition metal mediator, $Os(Me_2\text{-bpy})_3^{2+}$, which has an oxidation-reduction potential of about 0.47 V (vs. Ag/AgCl).

A number of labels that have been previously described for detection of binding interactions are not well-suited for use herein and are not included in this application. For example, omitted as labels for mediated electrochemical detection are transition metal complexes and enzyme labels that require a substrate to generate electrochemical or optical signal through enzymatic catalysis. In the mediated catalytic electrochemical detection of the invention, the transition metal complex acts as a catalyst and not as a label.

F. Assay Formats

The general method of detection of binding interactions of the instant invention as described above can take any one of several formats, including conventional sandwich assays, competitive assays, or assays with direct target detection. These assays maybe based on immunological affinity or on affinities that are based on receptor-ligand, protein-protein, or DNA-protein interactions. Cell receptors for proteins which can be used in the instant invention as binders include but are not limited to receptors for transport proteins (i.e., transferrin receptor) (Testa, U., et al., *Crit. Rev. Oncog.*, 1993, 4, 241), receptors for hormone/growth factors (i.e., epidermal growth factor, insulin, nerve growth factor) (Ullrich, A. et al., *Cell*, 1990, 61 203; Baxter, R. C., *Am. J. Physiol. Endocrinol. Metabol.*, 2000, 278, E967), and G-protein coupled receptors for hormones such as luteinizing hormone, follicle-stimulating hormone, and thyroid stimulating hormone (Schoneberg, T., et at., *Mol. Cell Endocrinolo.*, 1999, 151 181). Receptors of bacterial origin (Modun, B. J., et al., *Microbiology*, 1998, 144 1005; Schryvers, A. B., et al., *Adv. Exp. Med. Biol.*, 1998, 443 123) and viral origin (Bella, J., et al., *J. Struct. Biol*, 1999, 128 69; Domingo, E., et al., *Virus Res.*, 1999, 62 169) may also be used in the instant invention. Extracellular matrix proteins (ECM) can be used to detect ECM-binding proteins (Najjam, S., et al., *Cytokine*, 1997, 9 1013). DNA can be immobilized as a binding member for DNA-binding proteins such as transcription factors (activators, repressors, or regulators) (McGown, L. B., et al., *Anal. Chem.*, 1995, 67 663 A). Mediated electrochemical detection of binding interactions may also be utilized to evaluate drug candidates for their effects on protein-protein and other biological interactions. As such, the technology described here provides a versatile binding assay for drug discovery which can be applied to a variety of drag target-drug interactions. As used herein the tenn "target protein" includes proteins, glycoproteins, lipoproteins, protein fragments, polypeptides, glycoprotein fragments and lipoprotein fragments.

1. Sandwich

Briefly, in the sandwich assay format, the procedure consists of modifying the electrode with the first member of the binding pair (i.e., antibody, receptor, or DNA), adding the sample, which may or may not contain the target protein or target substance, then adding the second binding member, washing to remove unbound reagents, and adding mediator. Electrochemical interrogation is performed, and enhanced cyclic voltammetry or chronoamperometry signal relative to a control indicates the presence of the target protein or target substance in the sample.

In this format, the target in the sample is detected via capture by a solid-phase immobilized first binder, such as an antibody, antibody fragment, receptor protein or DNA to form a target complex, followed by the binding of the captured target by a labeled second binder to form a 3-member target complex. In a preferred embodiment, the second binder contains only endogenous labels (i.e., electrochemically active amino acids) and the presence of target in a sample is evident from the increased current generated by the target complex. In contrast, significantly less current is generated with samples not containing the target since complex formation does not occur, and thus, current is generated only by any endogenous label in the solid phase immobilized binder alone.

In a second preferred embodiment of the sandwich assay, the current generated by the first preferred embodiment is enhanced by the addition of a third binder that recognizes the second binder on the target complex to create a 4-member complex. This is analogous to the use of secondary binders in classical immunoassays. The preferred mediator for the first two embodiments (above) is Ru(bpy)$_3^{+2}$ which has a potential of about 1.05 V or OS(bpy)$_3^{+2}$ which has a potential of 0.65 V (vs. Ag/AgCl).

In a third preferred embodiment of the sandwich assay format, the second or third binder is covalently labeled with labels such as oligonucleotides, proteins, peptides, or peptides containing modified amino acids with lower redox potentials (approximately $\leq 0.6$ V vs. Ag/AgCl),. Mediators matched to these lower potentials, such as Os(Me$_2$bpy)$_3^{2+}$, are used with the low potential labels. In addition, the second or third binder may be labeled with certain electron donor compounds that also have low potentials.

In the instant invention, an alternative to the above sequence steps for the method of detection is to mix the sample with the second binder prior to exposure of the mixture to the immobilized first binder, such that the binding of the second binder occurs prior to binding of the target to the immobilized first binder.

2. Competitive

In the competitive assay format, the target competes with a labeled target for binding to an immobilized binder. For example, the beta chain of the hormone, human chorionic gonadotropin (hCG), can be labeled with a peptide rich in tyrosine or an oligonucleotide containing guanine and shown to bind to rabbit antibody specific for the beta chain of hCG. The detection of hCG in a sample is possible by the competition of the hCG with the labeled beta chain for the beta chain-specific antibody. In this scenario, the electrochemical signal is high in the absence of target hCG, and the electrochemical signal decreases if target hCG competes with the labeled beta-chain for the immobilized hCG beta chain-specific antibody. In a similar manner, a labeled surrogate target bound to an immobilized binder may be displaced by target present in a test sample, resulting in a decrease in electrochemical signal. The competitive format is particularly suitable for detecting binding interactions of small molecules such as drugs, steroids and vitamins (Example 7).

3. Direct

In the direct target detection assay, the steps are the same as for the sandwich assay except a labeled second binder is not added. The labeled second binder is not required in this case because the target protein has the property of being electrochemically active itself, and allows direct mediated electrochemical detection of the target. This approach can be used particularly for large proteins (i.e., $\geq 150$ kD), such as antibodies or other globulins that contain many amino acids and thus are able to generate a significant electrochemical current by themselves through a catalytic oxidation-reduction reaction with a mediator such as Ru(bpy)$_3^{+2}$.

4. Competitive Assay for Immobilized Target Substance

In this format, a target substance or surrogate target substance is immobilized on the electrode surface and exposed to the sample (which may or may not contain the target substance) and a labeled binder (either endogenous or exogenous). As is normally used in this art, for example, in drug discovery, the surrogate target substance has a lower binding affinity than the target substance for the labeled binder. In this embodiment of the invention, the electrochemical signal is high in the absence of the target substance in the sample due to the binding of the labeled binder to the immobilized surrogate target substance, and the electrochemical signal decreases if target substance present in the sample competes with the immobilized surrogate target substance for binding of the labeled binder.

5. Binding Interaction Assay

In this format, a first binder that is a member of a binding pair is immobilized on the electrode surface. The immobilized binder is exposed to a test sample and to a second binder that is a member of the binding pair in order to determine the effect of the test sample on the binding interaction between the first and second binders. The test sample may comprise a substance that facilitates, inhibits, or does not affect binding of the two binders. For example, the test sample could contain a drug candidate that prevents two proteins from binding to each other, or the test sample could contain a drug candidate that enhances the binding interaction. Thus, this assay format can be used to screen potential drug compounds in order to determine the effect they have on a binding interaction. The mode of action by which the test sample affects the binding interaction includes but is not limited to blocking or enhancing the binding of one of the binders and inducing a conformational change in the binding site. In contrast to the above assay formats where the intention is to detect the presence or absence of a substance using catalytic mediated electrochemistry, the binding interaction assay format is designed to detect the effect of a substance on a binding interaction between members of a binding pair using catalytic mediated electrochemistry.

The features of the present invention will be more clearly understood by reference to the following examples, which are not to be construed as limiting the invention.

EXAMPLES

Example 1

Electrochemical detection of tyrosine, tryptophan and 5-hydroxytryptophan in solution using mediated catalytic oxidation. The presence of tyrosine, tryptophan and 5-hydroxytryptophan was determined in a solution using cyclic voltammetry at a scan rate of 300 mV/s (FIGS. 1A–1C). The working, reference and counter electrodes were ITO, Ag/AgCl, and platinum wire, respectively. The substrate (amino acid) concentration was 100 $\mu$M, and the mediator concentration was 20 $\mu$M with 50 $\mu$mM sodium phosphate, pH 7.5 as the supporting electrolyte. The mediators used were A) Ru(bpy)$_3^{2+}$,B) Os(bpy)$_3^{2+}$, and C) Os(Me$_2$-bpy)$_3^{2+}$. A dramatic increase in the anodic (oxidative) current from the mediator in the presence of substrate provides a quantitative measure of the amount of substrate in solution based on the catalytic current enhancement due to reaction between the oxidized mediator and the substrate. The selective reactivity of the different mediators with the substrates (i.e., only 5-hydroxytyptophan is detected by Os(Me$_2$-bpy)$_3^{2+}$, both 5-hydroxytryptophan and tyrosine are detected by Os(bpy)$_3^{2+}$, and 5-hydroxytryptophan, tyrosine, and tryptophan are detected by Ru(bpy)$_3^{2+}$) demonstrates the selectivity of the mediated electrochemical detection technique.

Example 2

Attachment of an exogenous electrochemical label to a signal molecule. Electrochemical labels that contain a primary amine can be attached to other molecules that contain primary amines. An example of this method is the coupling of a peptide or oligonucleotide modified with an alkyl amine linker to lysine residues on an antibody using the heterobifunctional crosslinkers, N-succinimidyl-S-acetylthioacetate (SATA) and sulfosuccinimidyl-4-(N-maleimidomethyl) cyclohexane-1-carboxylate (sulfo-SMCC)(both from Pierce Chemical Co., Rockford, Ill.). Both of the crosslinkers contain an amino-reactive N-hydroxysuccinimide (NHS) ester; however, SATA possesses a protected thiol, while SMCC has a thiol-reactive maleimide functionality. Thus, once the label is modified with SATA and the antibody is modified with SMCC, the label and antibody can be covalently coupled under conditions in which the protected SATA thiol is liberated and reacts with the maleimide group of SMCC. A typical coupling procedure is described in detail in the instruction provided by the manufacturer with these reagents. In the present application, a label containing one primary amine (such as a peptide or oligonucleotide with an amino terminus) and an antibody are separately reacted with a 20-fold excess of SATA and sulfo-SMCC, respectively, for 2 hr at room temperature. Second, excess coupling reagent is removed from each reaction by gel filtration chromatography with G-25 Sephadex resin (Sigma, St. Louis, Mo.). Typically, the ratio of crosslinker incorporation is 1:1 for the label and 3–8:1 for the antibody. Third, the modified label and antibody are then reacted at a ratio of 10–20 SATA per SMCC for 2 hr at room temperature in the presence of 50 $\mu$mM hydroxylamine. Finally, the labeled antibody is separated from the excess free label by gel filtration or successive washes in a centrifugal concentration device.

Example 3

Figure 2:
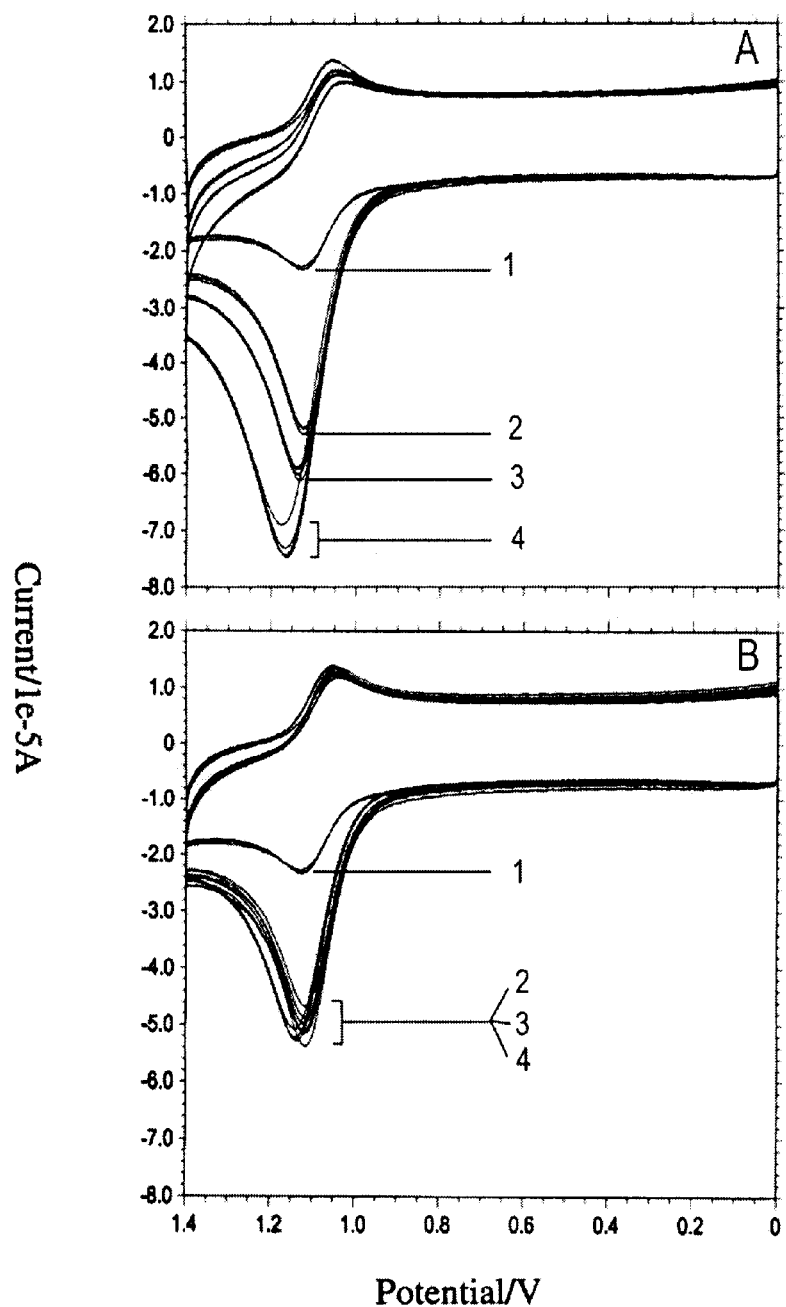
FIGS. 2A–2B. Electrochemical detection of passively adsorbed mouse IgG (FIG. 2A), but not human IgG (FIG. 2B), by the increased current generated following the sequential binding of two binders (i.e., antibodies). Following passive adsorption of either mouse or human IgG for 15 hr, ITO electrodes were blocked with 0.1% polyvinyl alcohol and were treated with a goat anti-mouse IgG (15 µg/ml) that had been affinity isolated on a mouse IgG column and subsequently adsorbed with human IgG to remove any cross reactivity to human IgG. This antibody was removed after a 2 hr. incubation, the ITO washed with PBS and then exposed to the second binder (rabbit anti-goat IgG at 15 µg/ml) for an additional 2 hr. Increased current generated over that seen by the oxidation of the passively adsorbed mouse IgG alone and over that seen with adsorbed human IgG after sequential incubation with both soluble binders was indicative of additional amino acid oxidation due to binding of both soluble binders when electrodes were coated with mouse IgG. Current changes were assessed using cyclic voltammetry (2.5 V/s) and the redox mediator, $Ru(bpy)_3^{2+}$, at 50 μM in 50 μM sodium phosphate, pH 7.0. Numbering of Treatment Sequences in FIG. 2.

Detection of passively bound protein (IgG) with two soluble binders —the first binder being specific for the IgG and the second binder being specific for the first binder. Mouse IgG (mIgG) and human IgG (hIgG) were passively adsorbed to ITO overnight as follows: Fifty microliters of a 50 $\mu$g/ml IgG solution in 50 $\mu$mM sodium acetate buffer, pH 5, was applied to 0.28 cm$^2$ areas of ITO delineated in a 96-well microtiter plate format. The ITO microtiter wells were formed by fusing a piece of ITO coated glass to the bottom of a 96-well microtiter plate upper portion. Protein adsorption was allowed to proceed for 15 hr. This was followed by treatment of ITO microtiter wells with 200 $\mu$l of 0.1% (w/v) 80% hydrolyzed polyvinyl alcohol (PVA) in 50 $\mu$mM sodium acetate, pH 5.8 for 2 hr at room temperature to block any unreacted binding sites on the ITO surface and on the polystyrene microtiter plate upper portion. After washing with PBS, the wells were treated for 2 hr with the first binder (goat anti-mouse IgG, 15 $\mu$g/ml, 100 $\mu$l/well) (Sigma Chemical). The goat anti-mouse IgG antibody had been affinity isolated on a mIgG column and adsorbed with human IgG to remove any reactivity specific for hIgG. After washing the ITO with PBS, the wells were treated for 2 hr with the second binder (rabbit anti-goat IgG, 15 $\mu$g/ml) (Sigma Chemical). Washed wells were subsequently evaluated using cyclic voltammetry (2.5 V/sec) with 50 $\mu$M Ru(bpy)$_3$ as redox mediator (FIGS. 2A–2B). As shown in FIG. 2A, the addition of the first binder to ITO with adsorbed mIgG resulted in a significant current increase over that seen with adsorbed mIgG alone (FIG. 2A #3 versus #2), indicating that the first binder was binding the mIgG. A further current increase was observed when incubation with the first binder was followed by incubation with the second binder (FIG. 2A #4 versus #3). None of these increases was observed when the same antibody combinations were applied to ITO adsorbed with hIgG (FIG. 2B).

Example 4

Figure 3:
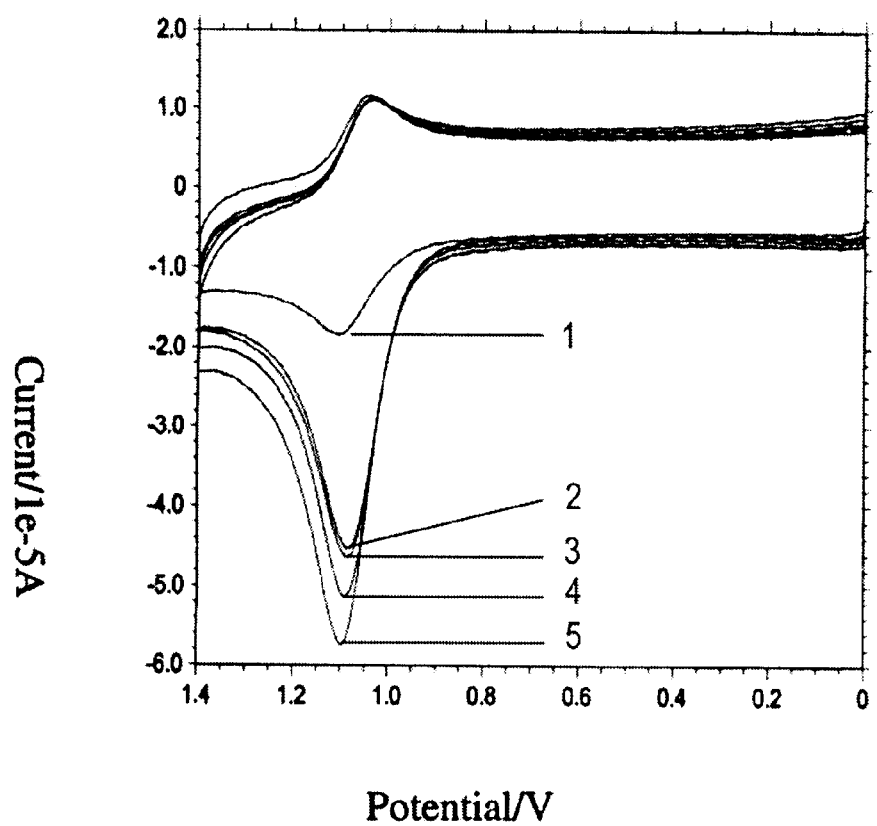
FIG. 3. Detection of human chorionic gonadotropin (hCG) hormone using an oligonucleotide-labeled antibody and mediated catalytic electrochemistry. ITO electrodes were modified by passively adsorbing 20 μg/ml rabbit anti-beta chain hCG IgG in 100 mM acetate buffer, pH 5.0, overnight, and were blocked with 0.1% polyvinyl alcohol. The modified electrodes were treated with 0, 10, or 50 ng/ml hCG, washed with phosphate buffered saline, and treated with 25 μg/ml goat anti-alpha chain hCG IgG labeled with five guanine-containing oligonucleotide labels per IgG in phosphate buffered saline. After washing the electrodes, cyclic voltammograms (2.5 V/s) were collected in the presence of 50 μM $Ru(bpy)_3^{2+}$ in 50 μmM phosphate buffer, pH 7.0. Numbering of Treatment Sequences in FIG. 3. #1, PVA block only; #2, rabbit anti-beta chain hCG IgG→PVA block→no hCG→goat anti-alpha chain hCG IgG labeled with oligonucleotide; #3, rabbit anti-beta chain hCG IgG→PVA block→50 ng/ml hCG→goat anti-alpha chain hCG IgG; #4, rabbit anti-beta chain hCG IgG→PVA block→10 ng/ml hCG→goat anti-alpha chain hCG IgG labeled with oligonucleotide; #5, rabbit anti-beta chain hCG IgG→PVA block→50 ng/ml hCG→goat anti-alpha chain hCG IgG labeled with oligonucleotide.

Electrochemical detection of human chorionic gonadotropin (hCG) antigen on an ITO electrode in a sandwich immunoassay using a signal antibody labeled with an exogenous oligonucleotide label. Electrochemical detection of hCG captured on the surface of an ITO electrode was demonstrated using ITO modified with a rabbit antibeta chain hCG capture antibody (Biostride, Inc., Redwood City, Calif.)(FIG. 3). Capture antibody was passively adsorbed onto ITO overnight from a solution of 20 $\mu$g/ml antibody in 50 mM sodium acetate, pH 5.0. The ITO was then blocked with 0.1% (w/v) 80% hydrolyzed polyvinyl alcohol (PVA) in 50 $\mu$mM sodium acetate, pH 5.8 for 2 hr at room temperature to reduce non-specific binding of the antigen and signal antibody. After blocking, the ITO was washed three times with phosphate buffered saline (PBS). The PVA-blocked, capture-antibody modified ITO was then treated with 0, 10, or 50 ng/ml hCG (Sigma) in PBS. After 2 hr incubation, the ITO electrodes were washed three times with PBS and treated with labeled and unlabeled goat anti-alpha chain hCG antibody (Biostride, Inc.) at 25 $\mu$g/ml in PBS. The label was a nine guanine-containing oligonucleotide and was present at a stoichiometry of five labels per signal IgG molecule. The ITO electrodes were then used to collect cyclic voltammograms in the presence of 50 $\mu$M Ru(bpy)$_3^{2+}$ in 50 $\mu$mM phosphate buffer, pH 7.0. The increased electrochemical signal from ITO exposed to hCG and the second labeled antibody (FIG. 3, #4 and #5) relative to ITO that was exposed to no hCG (FIG. 3, #2) indicates the specific electrochemical detection of hCG. The increased signal from labeled (FIG. 3, #4 and #5) versus unlabeled (FIG. 3, #3) second antibody in the presence of hCG reflects the signal enhancement obtained from the exogenous electrochemical label.

Example 5

Figure 4:
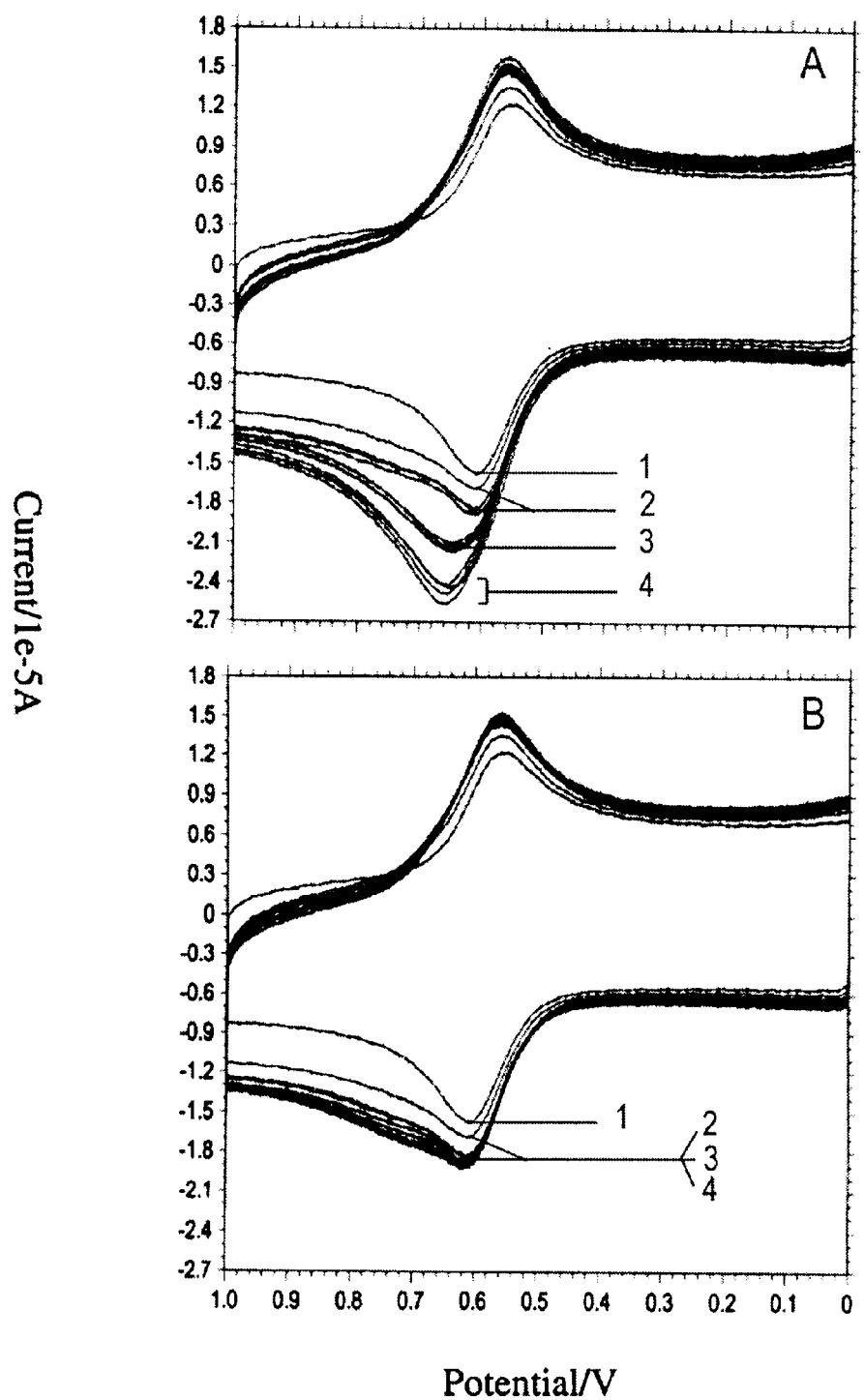
FIGS. 4A–4B. Detection of human chorionic gonadotropin (hCG) hormone using a peptide-labeled antibody and mediated catalytic electrochemistry. ITO electrodes were modified by passively adsorbing 20 μg/ml rabbit anti-beta chain hCG IgG in 100 mM acetate buffer, pH 5.0, overnight, and were blocked with 0.1% polyvinyl alcohol. The modified electrodes were treated with 100 ng/ml hCG, washed with phosphate buffered saline, and treated with 30 μg/ml goat anti-alpha chain hCG IgG labeled with five tyrosine-containing peptide labels per IgG in phosphate buffered saline for 1.5 hr. After washing the electrodes, cyclic voltammograms (2.5 V/s) were collected in the presence of 50 μM $Os(bpy)_3^{2+}$ in 50 μmM phosphate buffer, pH 7.0. Numbering of Treatment Sequences in FIG. 4.

Electrochemical detection of human chorionic gonadotropin (hCG) antigen on an ITO electrode in a sandwich immunoassay using a signal antibody labeled with an exogenous peptide label. Electrochemical detection of hCG captured on the surface of an ITO electrode was demonstrated using ITO modified with a rabbit anti-beta chain hCG capture antibody (Biostride, Inc., Redwood City, Calif.) (FIG. 4). Capture antibody was passively adsorbed onto ITO overnight from a solution of 20 $\mu$g/ml antibody in 50 mM sodium acetate, pH 5.0. The ITO was then blocked with 0.1% (w/v) 80% hydrolyzed polyvinyl alcohol (PVA) in 50 $\mu$mM sodium acetate, pH 5.8 for 2 hr at room temperature to reduce non-specific binding of the antigen and signal antibody. After blocking, the ITO was washed three times with phosphate buffered saline (PBS). The PVA-blocked, capture-antibody modified ITO was then treated with 100 ng/ml hCG (Sigma) in PBS. After 2 hr incubation, the ITO electrodes were washed three times with PBS and treated with labeled and unlabeled goat anti-alpha chain hCG antibody (Biostride, Inc.) at 30 $\mu$g/ml in PBS. The label was a five tyrosine-containing peptide and was present at a stoichiometry of five labels per signal IgG molecule. The ITO electrodes were then used to collect cyclic voltammograms in the presence of 50 $\mu$M Os(bpy)$_3^{2+}$ in 50 $\mu$mM phosphate buffer, pH 7.0. The increased electrochemical signal from ITO exposed to hCG and peptide labeled antibody (FIG. 4A, #4) relative to ITO that was exposed to no hCG (FIG. 4A, #3) indicates the specific electrochemical detection of hCG. The increased signal from labeled (FIG. 4A. #4) versus unlabeled (FIG. 4B, #4) second antibody reflects the signal enhancement from the exogenous label.

Example 6

Figure 5:
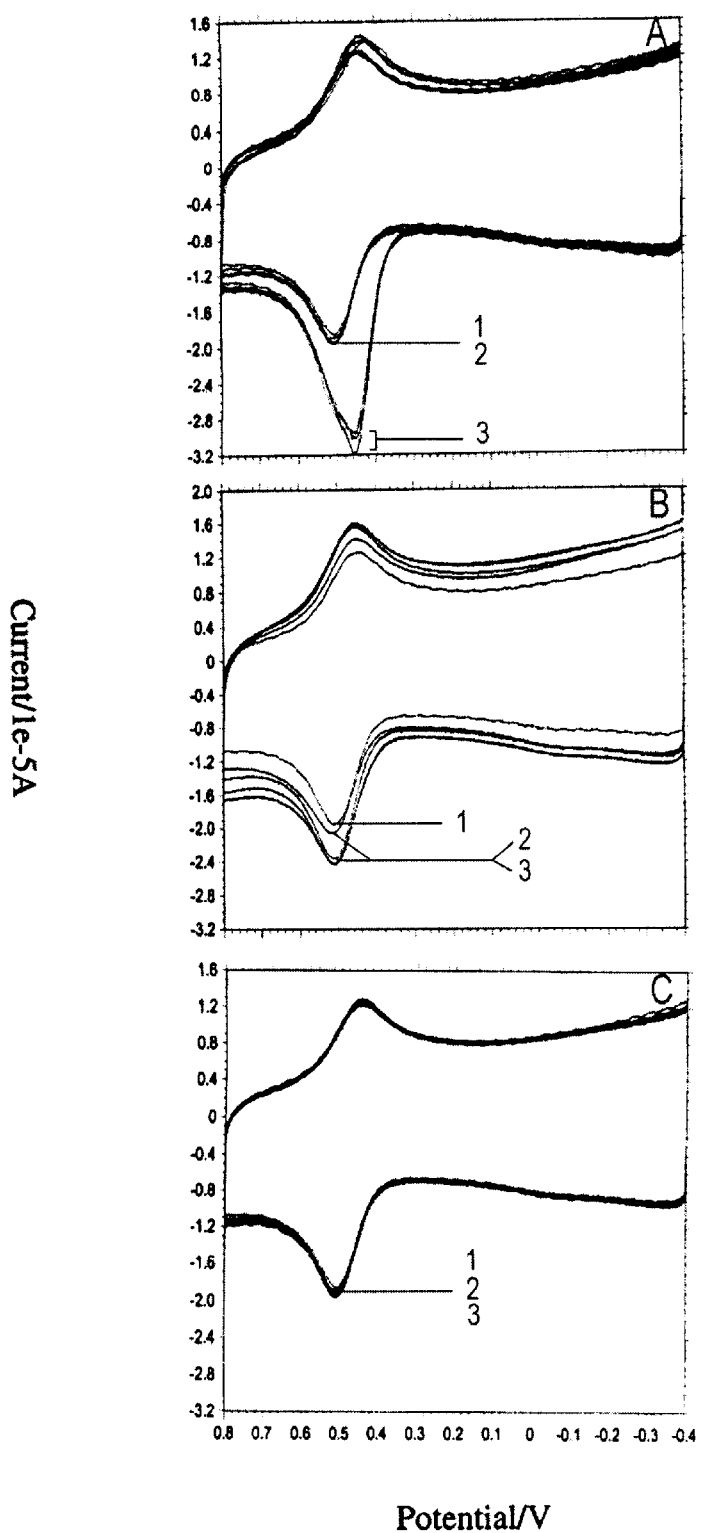
FIGS. 5A–5C. Detection of an affinity captured IgG labeled with a peptide containing the low potential amino acid 5-hydroxythyptophan. ITO electrodes were modified by passively adsorbing 20 μg/ml rabbit anti-goat IgG (Sigma Chemical) (FIGS. 5A,C) or, as a control, 20 μg/ml non-immune rabbit IgG (Sigma Chemical) (FIG. 5B) in 50 μmM acetate buffer, pH 5, for 15 hr. All the ITO electrodes were blocked with 0.1% polyvinyl alcohol. After washing, electrodes were exposed to 25 μg/ml peptide-labeled goat IgG (IgG-WOH) (FIGS. 5A,B) or the same unlabeled IgG (FIG. 5C). The peptide used for labeling was prepared by The American Peptide Co., Inc., Sunnyvale, Calif. Cyclic voltammograms (2.5 V/sec) were collected in duplicate in the presence of 50 μm $Os(Ne_2-bpy)_3^{2+}$ in 50 μmM phosphate buffer. Numbering of Treatment Sequences in FIG. 5.

Electrochemical detection of an IgG labeled with an exogenous peptide containing a modified low potential amino acid (5-hydroxytryptophan) and using the low potential mediator, Osmium$^{2+}$(4,4'-dimethyl-2,2'-bipyridine)$_3$ ("Os(Me$_2$-bpy)$_3$$^{2+}$") The exogenous peptide label was a 21-mer containing three 5-hydroxyntyptophan residues. The peptide labeled goat IgG (IgG-WOH) was captured with an affinity purified rabbit anti-goat IgG (Sigma Chemical) that was passively adsorbed on the ITO surface from a 50 mM sodium acetate buffer, pH 5. After adsorption (i.e., immobilization) of the capture IgG, the ITO was blocked with 0.1% (w/v) 80% hydrolyzed polyvinyl alcohol (PVA) (Sigma Chemical) in 50 mM sodium acetate, pH 5.8 for 2 hr at room temperature. ITO with capture IgG was treated with the IgG-WOH at 25 μg/ml for 4 hr (FIG. 5A). The ITO electrode was then used to collect the cyclic voltammograms in duplicate in the presence of 50 μm Os(Me$_2$-bpy)$_3$$^{2+}$ in 50 mM phosphate buffer, pH 7. As controls, ITO electrodes with non-immune rabbit IgG as capture were treated with IgG-WOH (FIG. 5B), and ITO electrodes with rabbit anti-goat IgG as capture were treated with unlabeled goat IgG (FIG. 5C). The increased electrochemical signal from ITO with rabbit anti-goat capture IgG exposed to IgG-WOH indicates electron transfer from the modified amino acid to the Os(Me$_2$-bpy)$_3$$^{2+}$ mediator (FIG. 5A). Little or no increase in the electrochemical signal is seen when nonimmune rabbit IgG was used instead of rabbit anti-goat IgG as capture (FIG. 5B) or when goat IgG was not labeled with the modified peptide (FIG. 5C). The use of this modified low potential amino acid as a label with the low potential mediator, Os(Me$_2$-bpy)$_3$$^{2+}$, permits protein detection with very low background signal from endogenous amino acids in the assay reagents or target proteins.

Example 7

Figure 6:
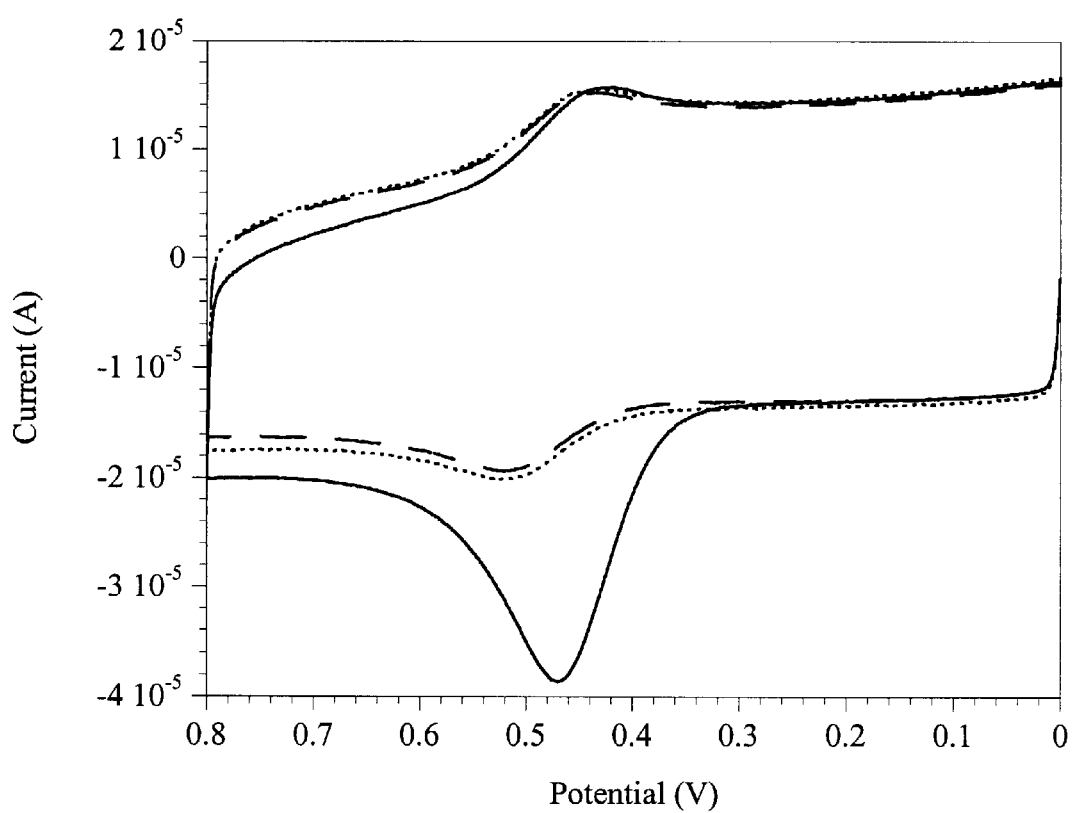
FIG. 6. Competitive assay for detection of biotin (vitamin H) in a sample using biotin labeled with a peptide containing 5-hydroxytryptophan. ITO electrodes were modified by passively adsorbing 20 μg/ml neutravidin in 100 μmM acetate buffer, pH 5.0 overnight and were blocked with 0.1% polyvinyl alcohol. The modified electrodes were treated with 1 μM biotin-peptide (—, —) in phosphate buffered saline, 1 μM biotin-peptide plus 160 μM free biotin (— — —) in phosphate buffered saline, or phosphate buffered saline alone ( . . . ). After washing the electrodes, cyclic voltammograms (2.5 V/s) were collected in the presence of 50 μmM $Os(Me_2-bpy)_3^{2+}$ in 50 μM phosphate buffer, pH 7.3. The 21-mer peptide label contained three 5-hydroxytryptophan residues.

Detection of biotin (vitamin H) in a competitive assay using labeled biotin. Electrochemical detection of biotin is demonstrated using ITO modified with neutravidin (Pierce Chemical Co., Rockford, Ill.) and biotin labeled with a peptide containing 5-hydroxytryptophan. (FIG. 6). Neutravidin was passively adsorbed onto ITO overnight, from a solution of 20 μg/ml neutravidin in 50 mM sodium acetate, pH 5.0. The ITO was then blocked with 0.1% (w/v) 80% hydrolyzed polyvinyl alcohol (PVA) (Sigma Chemical) in 50 mM sodium acetate, pH 5.8 for 2 hr at room temperature to reduce non-specific binding. After blocking, the ITO was washed three times with phosphate buffered saline (PBS). The PVA-blocked, neutravidin-modified ITO was then treated with PBS only (untreated), 1 μM labeled biotin in PBS, or 1 μM labeled biotin plus 160 μM unlabeled biotin in PBS. After 2 hr incubation, the ITO electrodes were washed with PBS, blotted dry, and used to collect cyclic voltammograms (2.5 V/s) in the presence of 50 μM Os(Me$_2$-bpy)$_3$$^{2+}$ in 50 mM phosphate buffer, pH 7.3. The results show a decrease in electrochemical signal from the sample containing unlabeled biotin indicating a decrease in the amount of labeled biotin bound on the surface of the ITO electrode due to the presence of unlabeled biotin in the sample. The 21-mer peptide label contained three 5-hydroxytryptophan residues.

While the invention has been described with reference to specific embodiments, it will be appreciated that numerous variations, modifications, and embodiments are possible, and accordingly, all such variations, modifications, and embodiments are to be regarded as being within the spirit and scope of the invention.

What is claimed is:

1. A method of determining the presence or absence of a target substance in a test sample, comprising:
   a) providing an electrode comprising a conductive substrate modified with a non-conductive layer having an immobilized first binder capable of binding the target substance and through which layer a transition metal mediator can freely move to transfer electrons to the conductive substrate;
   b) contacting the immobilized first binder with the test sample to form a target complex if the target substance is present in the test sample;
   c) contacting the first binder or the target complex, if present, with a second binder capable of binding the target substance and having an endogenous or exogenous label capable of being oxidized in an oxidation-reduction reaction;
   d) contacting the electrode, the immobilized first binder, and the target complex having the second binder, if present, with a transition metal mediator that oxidizes the label in an oxidation-reduction reaction between the transition metal mediator and the label, from which label there is electron transfer to the transition metal mediator resulting in regeneration of the reduced form of the transition metal mediator as part of a catalytic cycle;
   e) detecting the oxidation-reduction reaction; and
   f) determining the presence or absence of the target substance in the test sample from the detected oxidation-reduction reaction.

2. The method of claim 1, wherein the target substance is selected from the group consisting of proteins, protein fragments, ligands, carbohydrates, drugs, drug candidates and hormones.

3. The method of claim 1, wherein the immobilized first binder is selected from the group consisting of immunoglobulins, receptors, proteins, and oligonucleotides.

4. The method of claim 3, wherein the immobilized first binder is a receptor of eukaryotic, prokaryotic or viral origin.

5. The method of claim 3, wherein the immobilized first binder is an extracellular matrix protein.

6. The method of claim 1, wherein the second binder is labeled with an exogenous label.

7. The method of claim 6, wherein the label is an oligonucleotide.

8. The method of claim 1 or 6, wherein the label is a peptide containing amino acids capable of being oxidized in an oxidation-reduction reaction.

9. The method of claim 8, wherein the peptide label contains one or more amino acids capable of being oxidized in an oxidation-reduction reaction at approximately ≦0.6V.

10. The method of claim 9, wherein the transition metal mediator is osmium$^{2+}$(4,4'-dimethyl-2,2'-bipyridine)$_3$.

11. The method of claim 1, wherein the test sample and the second binder are added to the immobilized first binder simultaneously.

12. The method of claim 1, wherein the nonconductive layer is the immobilized first binder.

13. The method of claim 1, wherein the nonconductive layer to which the first binder is immobilized is selected from the group consisting of streptavidin, avidin, protein A, protein G, and antibodies.

14. The method of claim 1, wherein the nonconductive layer to which the first binder is immobilized is a silane molecule covalently attached to the conductive substrate, said silane molecule further being capable of forming a covalent bond with the first binder.

15. The method of claim 1, wherein the nonconductive layer to which the first binder is immobilized comprises one or more components.

16. The method of claim 2, wherein the target substance is a protein.

17. The method of claim 16, wherein the immobilized first binder is selected from the group consisting of immunoglobulins, receptors, proteins, and oligonucleotides.

18. The method of claim 17, wherein the immobilized first binder is a receptor of eukaryotic, prokaryotic or viral origin.

19. The method of claim 17, wherein the immobilized first binder is an extracellular matrix protein.

20. The method of claim 16, wherein the second binder is labeled with an exogenous label.

21. The method of claim 20, wherein the label is an oligonucleotide.

22. The method of claim 20, wherein the label is a peptide containing amino acids capable of being oxidized in an oxidation-reduction reaction.

23. The method of claim 22, wherein the peptide label contains one or more amino acids capable of being oxidized in an oxidation-reduction reaction at approximately $\leq 0.6V$.

24. The method of claim 23, wherein the transition metal mediator is $osmium^{2+}(4,4'-dimethyl-2,2'-bipyridine)_3$.

25. The method of claim 16, wherein the test sample and the second binder are added to the immobilized first binder simultaneously.

26. The method of claim 16, wherein the nonconductive layer is the immobilized first binder.

27. The method of claim 16, wherein the nonconductive layer to which the first binder is immobilized is selected from the group consisting of streptavidin, avidin, protein A, protein G, and antibodies.

28. The method of claim 16, wherein the nonconductive layer to which the first binder is immobilized is a silane molecule covalently attached to the conductive substrate, said silane molecule further capable of forming a covalent bond with the first binder.

29. The method of claim 16, wherein the nonconductive layer to which the first binder is immobilized comprises one or more components.

30. A method of determining the presence or absence of a target substance in a test sample, comprising:
  a) providing an electrode comprising a conductive substrate modified with a non-conductive layer having an immobilized binder capable of binding the target substance and through which layer a transition metal mediator can freely move to transfer electrons to the conductive substrate;
  b) contacting the immobilized binder with the test sample to form a target complex if the target substance is present in the test sample;
  c) contacting the immobilized binder with an endogenously or exogenously labeled substance capable of binding with the immobilized binder, such that binding of the labeled substance is inhibited if the target complex is present, and wherein the label is capable of being oxidized in an oxidation-reduction reaction;
  d) contacting the electrode, the immobilized binder, the target substance, and the labeled substance, if present, with a transition metal mediator that oxidizes the label in an oxidation-reduction reaction between the transition metal mediator and the label, from which label there is electron transfer to the transition metal mediator resulting in regeneration of the reduced form of the transition metal mediator as part of a catalytic cycle;
  e) detecting the oxidation-reduction reaction; and
  f) determining the presence or absence of the target substance in the test sample from the detected oxidation-reduction reaction.

31. The method of claim 30, wherein the target substance is selected from the group consisting of proteins, protein fragments, ligands, carbohydrates, drugs, drug candidates, steroids and hormones.

32. The method of claim 30, wherein the test sample and labeled substance are added to the immobilized binder simultaneously.

33. The method of claim 30, wherein the immobilized binder is selected from the group consisting of immunoglobulins, receptors, proteins, and oligonucleotides.

34. The method of claim 33, wherein the immobilized binder is a receptor of eukaryotic, prokaryotic or viral origin.

35. The method of claim 33, wherein the immobilized binder is an extracellular matrix protein.

36. The method of claim 30, wherein the label is an exogenous label.

37. The method of claim 36, wherein the label is an oligonucleotide.

38. The method of claim 36, wherein the label is a peptide containing amino acids capable of being oxidized in an oxidation-reduction reaction.

39. The method of claim 38, wherein the peptide label contains one or more amino acids capable of being oxidized in an oxidation-reduction reaction at approximately $\leq 0.6V$.

40. The method of claim 39, wherein the transition metal mediator is $osmium^{2+}(4,4'-dimethyl-2,2'-bipyridine)_3$.

41. The method of claim 30, wherein the labeled substance is selected from the group consisting of proteins, protein fragments, recombinant proteins and recombinant protein fragments, ligands, carbohydrates, drugs, drug candidates, steroids and hormones.

42. The method of claim 30, wherein the nonconductive layer is the immobilized binder.

43. The method of claim 30, wherein the nonconductive layer to which the binder is immobilized is selected from the group consisting of streptavidin, avidin, protein A, protein G, and antibodies.

44. The method of claim 30, wherein the nonconductive layer to which the binder is immobilized is a silane molecule covalently attached to the conductive substrate, said silane molecule further capable of forming a covalent bond with the binder.

45. The method of claim 30, wherein the nonconductive layer to which the binder is immobilized comprises one or more components.

46. The method of claim 31, wherein the target substance is a protein.

47. The method of claim 46, wherein the test sample and the labeled substance are added to the immobilized binder simultaneously.

48. The method of claim 46, wherein the immobilized binder is selected from the group consisting of immunoglobulins, receptors, proteins, and oligonucleotides.

49. The method of claim 48, wherein the immobilized binder is a receptor of eukaryotic, prokaryotic or viral origin.

50. The method of claim 48, wherein the immobilized first binder is an extracellular matrix protein.

51. The method of claim 46, wherein the label is an exogenous label.

52. The method of claim 51, wherein the label is an oligonucleotide.

53. The method of claim 51, wherein the label is a peptide containing amino acids capable of being oxidized in an oxidation-reduction reaction.

54. The method of claim 53, wherein the peptide label contains one or more amino acids capable of being oxidized in an oxidation-reduction reaction at approximately ≦0.6V.

55. The method of claim 54, wherein the transition metal mediator is osmium$^{2+}$(4,4'-dimethyl-2,2'-bipyridine)$_3$.

56. The method of claim 46, wherein the labeled substance is selected from the group consisting of proteins and recombinant proteins.

57. The method of claim 46, wherein the nonconductive layer is the immobilized binder.

58. The method of claim 46, wherein the nonconductive layer to which the binder is immobilized is selected from the group consisting of streptavidin, avidin, protein A, protein G, and antibodies.

59. The method of claim 46, wherein the nonconductive layer to which the binder is immobilized is a silane molecule covalently attached to the conductive substrate, said silane molecule further capable of forming a covalent bond with the binder.

60. The method of claim 46, wherein the nonconductive layer to which the binder is immobilized comprises one or more components.

61. A method of determining the presence or absence of a target substance in a test sample, comprising:
   a) providing an electrode comprising a conductive substrate modified with a non-conductive layer having an immobilized binder capable of binding the target substance and through which layer a transition metal mediator can freely move to transfer electrons to the conductive substrate;
   b) contacting the immobilized binder with a surrogate target capable of binding with the immobilized binder to form a target complex, said surrogate target having an endogenous or exogenous label capable of being oxidized in an oxidation-reduction reaction;
   c) contacting the target complex with the test sample, so that labeled surrogate target is displaced from the immobilized binder by the target substance, if the target substance is present in the test sample;
   d) contacting the electrode, the immobilized binder, and said surrogate target, if present, with a transition metal mediator that oxidizes the label in an oxidation-reduction reaction between the transition metal mediator and the label, from which label there is electron transfer to the transition metal mediator resulting in regeneration of the reduced form of the transition metal mediator as part of a catalytic cycle;
   e) detecting the oxidation-reduction reaction; and
   f) determining the presence or absence of the target substance in the test sample from the detected oxidation-reduction reaction.

62. The method of claim 61, wherein the target substance is selected from the group consisting of proteins, protein fragments, ligands, carbohydrates, drugs, drug candidates, steroids and hormones.

63. The method of claim 61, wherein the immobilized binder is selected from the group consisting of immunoglobulins, receptors, proteins, and oligonucleotides.

64. The method of claim 63, wherein the immobilized binder is a receptor of eukaryotic, prokaryotic or viral origin.

65. The method of claim 63, wherein the immobilized binder is an extracellular matrix protein.

66. The method of claim 61, wherein the label is an exogenous label.

67. The method of claim 66, wherein with the label is an oligonucleotide.

68. The method of claim 66, wherein the label is a peptide containing amino acids capable of being oxidized in an oxidation-reduction reaction.

69. The method of claim 68, wherein the peptide label contains one or more amino acids capable of being oxidized in an oxidation-reduction reaction at approximately ≦0.6V.

70. The method of claim 69, wherein the transition metal mediator is osmium$^{2+}$(4,4'-dimethyl-2,2'-bipyridine)$_3$.

71. The method of claim 61, wherein the labeled surrogate target is selected from the group consisting of proteins, protein fragments, recombinant proteins and recombinant protein fragments, ligands, carbohydrates, drugs, drug candidates, steroids and hormones.

72. The method of claim 61, wherein the nonconductive layer is the immobilized binder.

73. The method of claim 61, wherein the nonconductive layer to which the binder is immobilized is selected from the group consisting of streptavidin, avidin, protein A, protein G, and antibodies.

74. The method of claim 61, wherein the nonconductive layer to which the binder is immobilized is a silane molecule covalently attached to the conductive substrate, said silane molecule further capable of forming a covalent bond with the binder.

75. The method of claim 61, wherein the nonconductive layer to which the binder is immobilized comprises one or more components.

76. A method of determining the presence or absence of a target substance in a test sample comprising:
   a) providing an electrode comprising a conductive substrate modified with a non-conductive layer having an immobilized target substance or an immobilized surrogate target substance, and through which layer a transition metal mediator can freely move to transfer electrons to the conductive substrate;
   b) contacting the immobilized target substance or immobilized surrogate target substance with the test sample and with an endogenously or exogenously labeled binder that will bind the target substance in the test sample such that the target substance in the test sample, if present, competes with the immobilized target substance or the immobilized surrogate target substance for the labeled binder, said label being capable of being oxidized in an oxidation-reduction reaction;
   c) contacting the electrode, the immobilized target substance or immobilized surrogate target substance, and the labeled binder, if present, with a transition metal mediator that oxidizes the label in an oxidation-reduction reaction between the transition metal mediator and the label, from which label there is electron transfer to the transition metal mediator resulting in regeneration of the reduced form of the transition metal mediator as part of a catalytic cycle;
   d) detecting the oxidation-reduction reaction; and
   e) determining the presence or absence of target substance in the test sample from the detected oxidation-reduction reaction.

77. The method of claim 76, wherein the target substance is selected from the group consisting of proteins, protein fragments, ligands, carbohydrates, drugs, drug candidates, steroids and hormones.

78. The method of claim 76, wherein the labeled binder and the test sample are mixed prior to being added to the immobilized target substance or immobilized surrogate target substance.

79. The method of claim 76, wherein the nonconductive layer is the immobilized target substance or immobilized surrogate target substance.

80. The method of claim 76, wherein the immobilized target substance or immobilized surrogate target substance is selected from the group consisting of proteins and recombinant proteins.

81. The method of claim 76, wherein the labeled binder is selected from the group consisting of inununoglobulins, receptors, proteins, and oligonucleotides.

82. The method of claim 81, wherein the labeled binder is a receptor of eukaryotic, prokaryotic or viral origin.

83. The method of claim 81, wherein the labeled binder is an extracellular ma trix protein.

84. The method of claim 81, wherein the label is an exogenous label.

85. The method of claim 84, wherein with the label is an oligonucleotide.

86. The method of claim 84, wherein the label is a peptide containing amino acids capable of being oxidized in an oxidation-reduction reaction.

87. The method of claim 86, wherein the peptide label contains one or more amino acids capable of being oxidized in an oxidation-reduction reaction at approximately $\leq 0.6V$.

88. The method of claim 87, wherein the transition metal mediator is osmium$^{2+}$(4,4'-dimethyl-2,2'-bipyridine)$_3$.

89. The method of claim 76, wherein the nonconductive layer to which the immobilized target substance or immobilized surrogate target substance is immobilized is selected from the group consisting of streptavidin, or avidin, protein A, protein G and antibodies.

90. The method of claim 76, wherein the nonconductive layer to which the immobilized target substance or immobilized surrogate target substance is immobilized is a silane molecule covalently attached to the conductive substrate, said silane molecule further capable of forming a covalent bond with the immobilized target substance or immobilized surrogate target substance.

91. The method of claim 76, wherein the nonconductive layer comprises one or more components.

92. A method of determining the effect of a test sample on the binding interactions between two binders that are members of a binding pair, said method comprising:
   a) providing an electrode comprising a conductive substrate modified with a non-conductive layer having an immobilized first binder and through which layer a transition metal mediator can freely move to transfer electrons to the conductive substrate;
   b) contacting the immobilized first binder with the test sample;
   c) contacting the immobilized first binder with an endogenously or exogenously labeled second binder for said first binder, said label being capable of being oxidized in an oxidation-reduction reaction;
   d) contacting the electrode, the immobilized first binder, and the labeled second binder, if present, with a transition metal mediator that oxidizes the label in an oxidation-reduction reaction between the transition metal mediator and the label, from which label there is electron transfer to the transition metal mediator resulting in regeneration of the reduced form of the transition metal mediator as part of a catalytic cycle;
   e) detecting the oxidation-reduction reaction; and
   f) determining the effect of the test sample on the ability of the second binder to bind to the first binder from the detected oxidation-reduction reaction.

93. The method of claim 92, wherein the test sample, the first binder and the second binder are each selected from the group consisting of proteins, protein fragments, recombinant proteins, recombinant protein fragments, extracellular matrix proteins, ligands, carbohydrates, steroids, hormones, drugs, drug candidates, immunoglobulins, receptors of eukaryotic, prokaryotic or viral origin, and oligonucleotides.

94. The method of claim 92, wherein the test sample and the labeled second binder are added to the immobilized first binder simultaneously.

95. The method of claim 92, wherein the labeled second binder is added to the immobilized first binder before the addition of the test sample to determine the effect of the test sample on the binding interactions between the first binder and the second binder.

96. The method of claim 92, wherein the label is an exogenous label.

97. The method of claim 96, wherein the label is an oligonucleotide.

98. The method of claim 96, wherein the label is a peptide containing amino acids capable of being oxidized in an oxidation-reduction reaction.

99. The method of claim 98, wherein the peptide label contains one or more amino acids capable of being oxidized in an oxidation-reduction reaction at approximately $\leq 0.6$ V.

100. The method of claim 99, wherein the transition metal mediator is osmium$^{2+}$(4,4'-dimethyl-2,2'-bipyridine)$_3$.

101. The method of claim 92, wherein the nonconductive layer is the immobilized first binder.

102. The method of claim 92, wherein the nonconductive layer to which the first binder is immobilized is selected from the group consisting of streptavidin, avidin, protein A, protein G, and antibodies.

103. The method of claim 92, wherein the nonconductive layer to which the first binder is immobilized is a silane molecule covalently attached to the conductive substrate, said silane molecule further capable of forming a covalent bond with the first binder.

104. The method of claim 92, wherein the nonconductive layer to which the first binder is immobilized comprises one or more components.

105. A method of determining the presence or absence of a target protein in a test sample, said target protein having an endogenous label capable of being oxidized in an oxidation-reduction reaction, comprising:
   a) providing an electrode comprising a conductive substrate modified with a non-conductive layer having an immobilized binder capable of binding the target protein and through which layer a transition metal mediator can freely move to transfer electrons to the conductive substrate;
   b) contacting the immobilized binder with the test sample to form a target complex if the target protein is present in the test sample;
   c) contacting the electrode, the immobilized binder and the target protein, if present, with a transition metal mediator that oxidizes the label in an oxidation-reduction reaction between the transition metal mediator and the label, from which label there is electron transfer to the transition metal mediator resulting in regeneration of the reduced form of the transition metal mediator as part of a catalytic cycle;
   d) detecting the oxidation-reduction reaction; and
   e) determining the presence or absence of the target protein in the test sample from the detected oxidation-reduction reaction.

106. The method of claim 105, wherein the immobilized binder is selected from the group consisting of immunoglobulins, receptors, proteins, and oligonucleotides.

107. The method of claim 106, wherein the immobilized binder is a receptor of eukaryotic, prokaryotic or viral origin.

108. The method of claim 106, wherein the immobilized binder is an extracellular matrix protein.

109. The method of claim 105, wherein the nonconductive layer is the immobilized binder.

110. The method of claim 105, wherein the nonconductive layer to which the binder is immobilized is selected from the group consisting of streptavidin, avidin, protein A, protein G, and antibodies.

111. The method of claim 105, wherein the nonconductive layer to which the binder is immobilized is a silane molecule covalently attached to the conductive substrate, said silane molecule further capable of forming a covalent bond with the binder.

112. The method of claim 105, wherein the nonconductive layer to which the binder is immobilized comprises one or more components.

* * * * *